(12) United States Patent
Jeffords et al.

(10) Patent No.: US 12,263,160 B2
(45) Date of Patent: *Apr. 1, 2025

(54) METHODS OF TREATING OCULAR INFLAMMATORY DISEASES

(71) Applicant: Iolyx Therapeutics, Inc., Burlingame, CA (US)

(72) Inventors: Elizabeth W. Jeffords, Hillsborough, CA (US); Hovhannes John Gukasyan, Orange, CA (US); Rozemarijn Verhoeven, Siler City, NC (US); Houman David Hemmati, Santa Monica, CA (US); Daniel J. Estes, San Diego, CA (US); Richard Graham, Irvine, CA (US)

(73) Assignee: IOLYX THERAPEUTICS, INC., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/950,802

(22) Filed: Sep. 22, 2022

(65) Prior Publication Data

US 2023/0090417 A1 Mar. 23, 2023

Related U.S. Application Data

(60) Provisional application No. 63/247,174, filed on Sep. 22, 2021, provisional application No. 63/251,874, filed on Oct. 4, 2021.

(51) Int. Cl.
| | | |
|---|---|---|
| *A61K 31/4468* | (2006.01) | |
| *A61K 31/335* | (2006.01) | |
| *A61K 31/573* | (2006.01) | |
| *A61P 27/02* | (2006.01) | |

(52) U.S. Cl.
CPC ........ *A61K 31/4468* (2013.01); *A61K 31/335* (2013.01); *A61K 31/573* (2013.01); *A61P 27/02* (2018.01)

(58) Field of Classification Search
CPC .............. A61K 31/335; A61K 31/4468; A61K 31/573; A61P 27/02
See application file for complete search history.

(56) References Cited

U.S. PATENT DOCUMENTS

| | | | |
|---|---|---|---|
| 5,712,298 A | 1/1998 | Amschler | |
| 6,872,382 B1 | 3/2005 | Gamache et al. | |
| 7,576,069 B2 | 8/2009 | Rieger et al. | |
| 7,605,143 B2 | 10/2009 | Rieger et al. | |
| 8,497,379 B2 | 7/2013 | Choi-Sledeski et al. | |
| 8,614,210 B2 | 12/2013 | Bhutada et al. | |
| 8,663,694 B2 | 3/2014 | Brück-Scheffler et al. | |
| 9,115,133 B2 | 8/2015 | Barawkar et al. | |
| 9,192,623 B2 | 11/2015 | Scott | |
| 2002/0035264 A1 | 3/2002 | Kararli et al. | |
| 2006/0084684 A1 | 4/2006 | Bolle et al. | |
| 2006/0257486 A1 | 11/2006 | Owen et al. | |
| 2007/0259009 A1 | 11/2007 | Linder | |
| 2008/0255209 A1 | 10/2008 | Klein et al. | |
| 2009/0186923 A1 | 7/2009 | Armer et al. | |
| 2009/0209599 A1* | 8/2009 | Endo ..................... A61K 9/0048 514/352 |
| 2011/0086023 A1 | 4/2011 | Lane | |
| 2012/0283252 A1 | 11/2012 | Bhutada et al. | |
| 2015/0125539 A1 | 5/2015 | Popov et al. | |
| 2015/0272936 A1 | 10/2015 | Vakkalanka et al. | |
| 2015/0366890 A1 | 12/2015 | Collins et al. | |
| 2016/0045508 A1 | 2/2016 | Vazquez et al. | |
| 2020/0129461 A1 | 4/2020 | Bannister et al. | |
| 2021/0244718 A1 | 8/2021 | Osborne | |
| 2021/0346661 A1 | 11/2021 | Johnson et al. | |
| 2022/0249451 A1* | 8/2022 | Chaudhuri ............. A61K 47/02 |
| 2023/0088371 A1* | 3/2023 | Graham ................. A61K 47/38 424/427 |

FOREIGN PATENT DOCUMENTS

| | | |
|---|---|---|
| EP | 1796668 B1 | 9/2008 |
| EP | 1906916 B1 | 10/2008 |
| EP | 1511516 B1 | 12/2008 |
| EP | 2020243 A1 | 2/2009 |
| EP | 1511481 B1 | 10/2010 |
| EP | 2020243 B1 | 8/2018 |

(Continued)

OTHER PUBLICATIONS

International Search Report and the Written Opinion of the International Searching Authority, issued in corresponding International Application No. PCT/US2022/076726, dated Nov. 25, 2022, 20 pages.

International Search Report and the Written Opinion of the International Searching Authority, issued in corresponding International Application No. PCT/US2022/076876, dated Dec. 15, 2022, 17 pages.

Cholkar et al. "Novel Strategies for Anterior Segment Ocular Drug Delivery," Journal of Ocular Pharmacology and Therapeutics, vol. 29, No. 2, Mar. 13, 2013, pp. 106-123.

Walscheid et al., "Increased Circulating Proinflammatory T Lymphocytes in Children with Different Forms of Anterior Uveitis: Results from a Pilot Study," (2019) Ocular Immunology and Inflammation, 27:5, 788-797, DOI: 10.1080/09273948.2018.1467464, 11 pages.

(Continued)

*Primary Examiner* — Kara R. McMillian
(74) *Attorney, Agent, or Firm* — Rothwell, Figg, Ernst & Manbeck, P.C.

(57) ABSTRACT

The present invention relates to methods of treating ocular inflammatory diseases by administering ophthalmic pharmaceutical compositions of roflumilast. Administration of ophthalmic pharmaceutical compositions of roflumilast can provide significant immunomodulatory and anti-inflammatory activity relative to existing immunomodulatory, immunosuppressant, or non-steroidal anti-inflammatory therapies, including corticosteroids and antihistamines, while also providing an improved safety and convenience profile relative to one or both agents.

21 Claims, 11 Drawing Sheets

(56) References Cited

FOREIGN PATENT DOCUMENTS

| WO | 9841232 A2 | 9/1998 | | |
|----|-----------|--------|----|----|
| WO | WO-03099278 A1 | * | 12/2003 | ............. A61K 31/44 |
| WO | 2006032675 A1 | 3/2006 | | |
| WO | 2006121963 A2 | 11/2006 | | |
| WO | 2015132708 A1 | 9/2015 | | |
| WO | 2017072131 A1 | 5/2017 | | |
| WO | 2021100051 A1 | 5/2021 | | |

OTHER PUBLICATIONS

Sakkas et al., "Phosphodiesterase 4 Inhibitors in Immune-mediated Diseases: Mode of Action, Clinical Applications, Current and Future Perspectives," Current Medicinal Chemistry (2017), 24, 3054-3067.

Tan et al., "Analysis of Th17-associated cytokines in tears of patients with dry eye syndrome," Eye (2014), 28, 608-613.

Liu et al., "Analysis of Th17-associated cytokines and clinical correlations in patients with dry eye disease," PLOS One 12(4) (Apr. 5, 2017), 12 pages.

Riemens et al., "Cytokines in tear fluid of patients with ocular graft-versus-host disease after allogeneic stem cell transplantation," Molecular Vision (2012), 18:797-802.

Rajasagi et al., "The Role of T Cells in Herpes Stromal Keratitis," Frontiers in Immunology, (Mar. 2019), vol. 10, Article 512, 7 pages.

Walscheid et al., "Increased Circulating Proinflammatory T Lymphocytes in Children with Different Forms of Anterior Uveitis: Results from a Pilot Study," Ocul Immunol Inflamm. (2019), 27(5):788-797, 2 pages.

Fung et al., "Local delivery of corticosteroids in clinical ophthalmology: A review," Clin. Experiment Ophthalmol. (2020), 48:366-401.

Kaiko et al., "Immunological decision-making: how does the immune system decide to mount a helper T-cell response?," Immunology, (Mar. 2008); 123(3): 326-338.

Kim et al., "Tear cytokines and chemokines in patients with Demodex blepharitis," Cytokine, 53, (2011), 94-99.

Allergan, Prescribing Information for Pred Forte (prednisolone acetate ophthalmic suspension, USP) 1% sterile (2017), 5 pages.

Agarwal et al., "Formulation Considerations for the Management of Dry Eye Disease," Pharmaceutics, 13, 207 (Feb. 3, 2021), 19 pages.

Non Final Office Action mailed Oct. 26, 2023 in corresponding U.S. Appl. No. 17/948,550, First Named Inventor: Richard Graham (24 pages).

Non-Final Office Action mailed Feb. 16, 2024 in corresponding U.S. Appl. No. 17/668,858, First Named Inventor: Bhaskar Chaudhuri (9 pages).

Loch, et al., "Determination of permeability coefficients of ophthalmic drugs through different layers of porcine, rabbit and bovine eyes", European Journal of Pharmaceutical Sciences 47 (2012) 131-138. (8 pages).

Toropainen, et al., "Biopharmaceutics of Topical Ophthalmic Suspensions: Importance of Viscosity and Particle Size in Ocular Absorption of Indomethacin", Pharmaceutics 2021, 13, 452. (13 pages).

Non-Final Office Action mailed Jun. 14, 2024 in corresponding U.S. Appl. No. 17/948,550, First Named Inventor: Richard Graham (13 pages).

Wiley A Chambers, MD. Clinical Review #2 for NDA 208144. Feb. 27, 2017. (Year: 2017)(6 pages).

Kalepu et al., "Review. Insoluble drug delivery strategies: review of recent advances and business prospects." Acta Pharmaceutica Sinica B 2015;5(5):442-453 (Year: 2015)(12 pages).

Mohr et al., "Gamma irradiation for terminal sterilization of 17β-estradiol loaded poly-( D,L-lactide-co-glycolide) microparticles." Journal of Controlled Release 61 (1999) 203-217 (Year: 1999)(15 pages).

* cited by examiner

METHODS OF TREATING OCULAR INFLAMMATORY DISEASES

CROSS REFERENCE TO RELATED APPLICATIONS

The present application claims priority to U.S. Provisional Application No. 63/247,174 filed on Sep. 22, 2021 and U.S. Provisional Application No. 63/251,874 filed on Oct. 4, 2021. Each of these applications is incorporated by reference herein.

FIELD OF THE INVENTION

The present invention includes methods of treating ocular inflammatory diseases by administering ophthalmic pharmaceutical compositions of roflumilast. The inventors of the subject application have surprisingly discovered that administration of ophthalmic pharmaceutical suspensions of roflumilast can provide significant anti-inflammatory activity relative to existing immunosuppressive and immunomodulatory therapies, including corticosteroids and antihistamines, while also providing an improved safety profile and convenience relative to one or both agents.

BACKGROUND OF THE INVENTION

Roflumilast is a potent and selective long-acting inhibitor of phosphodiesterase (PDE) type 4, with anti-inflammatory and potential antineoplastic activities. Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g., bronchitis, asthma, COPD), dermatoses (e.g., proliferative, inflammatory, and allergen induced skin disorders), and generalized inflammations in the gastrointestinal region (Crohn's disease and ulcerative colitis). Oral pharmaceutical compositions of roflumilast are currently marketed under the tradenames Daliresp® (in the United States) and Daxas® (in Europe) for COPD, and topical compositions of roflumilast cream for dermatological use are currently marketed under the tradename Zoryve™ (in the United States) for psoriasis.

Roflumilast and its synthesis are described in U.S. Pat. No. 5,712,298. It has been recognized that pharmaceutical compounds having phosphodiesterase (PDE)-4 inhibiting properties, such as roflumilast, are therapeutically effective and useful for treating inflammatory disorders, such as psoriasis and atopic dermatitis. While the therapeutic effectiveness of oral and dermal pharmaceutical compositions have been studied, there is a need for ophthalmic pharmaceutical compositions of roflumilast suitable for treating inflammatory or immune-mediated disorders of the eye. The majority of the market for anti-inflammatory ocular drugs today is based around antibiotics/anti-microbials (in the context of infectious/inflammatory indications), immunosuppressants (including corticosteroids), immunomodulatory agents (including antihistamines), and non-steroidal anti-inflammatory agents. These main classes of agents typically do not meet the clinical needs of mid to long-term inflammatory or immune-mediated disease, or present significant comorbidity and safety issues. As such, there is a high unmet need for an anti-inflammatory roflumilast ophthalmic formulation in a convenient and tolerable form.

The delivery of drugs to the eye is very difficult, as pharmaceutical ophthalmic agents must balance tolerability, sterility, safety, and efficacy. Priyanka Agarwal et al., *Formulation Considerations for the Management of Dry Eye Disease*, Pharmaceutics, 13, 207 (Feb. 3, 2021) discusses the formulation challenges for ophthalmic pharmaceutical formulations. For example, there can be poor tolerability of formulation excipients. Additionally, poor patient compliance is frequently a challenge with ophthalmic pharmaceutical formulations. Developing a stable ophthalmic formulation which can be made under sterile conditions while retaining physico-chemical properties of the active agent, staying within a tight range of pH and inactive ingredients which are tolerable to the eye, and which can be delivered in effective doses to the eye is very difficult. Ophthalmic delivery is focused on either the ocular surface, the anterior, or posterior segment of the eye. Ocular surface formulations, often delivered by the patient one to four or more times a day, have the additional challenge of requiring dosing consistency and yet flexibility to deliver effective dose despite common operator errors found in home-based patient delivery: sterility issues, variance in delivery volume, and accuracy in placement. Patients with long-term ocular disease also have increased sensitivity to active and inactive ingredients and preservatives, creating additional formulation challenges.

Ocular Surface Diseases (OSDs) are predominantly treated with three main categories of therapeutic ophthalmic pharmaceutical agents: immunomodulatory agents, immunosuppressants (including corticosteroids), antimicrobials, and non-steroidal anti-inflammatories (NSAID's). Each has their place, and yet all come with challenges. Corticosteroids, an immunosuppressant therapeutic approach for ophthalmic disease, although effective in dampening inflammatory activity, have long been known for their side effects, whether used in systemic, topical ophthalmic, or intraocular ophthalmic treatment, and often have to be dosed frequently. Antibiotics are highly effective for bacterial infections, which can drive certain OSDs, but diseases of an inflammatory nature are often misdiagnosed as purely bacterial in nature, and as such, anti-bacterial agents are often overused, leading to antibiotic and anti-microbial resistance, a long-term public health challenge, as well as inadequate treatment of the inflammation or the underlying autoimmune or immune-mediated ophthalmic condition. Non-steroidal immunomodulatory or immunosuppressive agents (including anti-histamines, anti-integrins, and calcineurin inhibitors) and non-steroidal anti-inflammatory agents (including bromfenac, diclofenac and others) also play a role in the treatment of inflammatory- or immune-driven ophthalmic disease, although they are often perceived as having limited utility, due to either a limited efficacy due to small set of immune targets (cellularly or based on location within the eye) or a challenging safety or tolerability profile. The challenges with all of the present standard of care immune and inflammatory-focused therapeutic agents leave a large unmet need for an alternative class of agents to directly address the underlying drivers of diseases of the eye, with high efficacy and yet lower patient- or population-based side effects, and higher convenience. In particular, prior to the present invention, there was a high unmet need for an anti-inflammatory pharmaceutical agent with a broad-spectrum mechanism of action targeting the most frequent but multi-faceted underlying drivers of inflammatory and immune-mediated eye disease, but with few systemic or ocular side effects, and less frequent dosing.

Corticosteroids are one of the most frequently used classes of ocular pharmaceutical agents, often administered as an agent of first and last resort in inflammatory diseases of the eye with a non-infectious etiology, or used in combination with anti-microbial agents in diseases also suspected of an infectious etiology. Corticosteroids are typically relatively effective with a relatively short onset of action, can be administered in a multitude of formulations: topical suspensions, gels, ointments, injections or depots; and can be administered in co-formulations with antibiotics or other targeted pharmaceutical agents. And yet, much like with their use in dermatological, immunological, auto-immune, and a host of other disease states; corticosteroids, even in short-term settings, come with a variety of profound local and systemic side effects. Corticosteroid use in the eye can locally decrease wound healing, increase susceptibility to or reactivate fungal or viral infections (and in fact can even increase the risk of direct endophthalmitis or other infections when delivered improperly in unsterile conditions), cause tissue specific side effects such as thinning of epithelial tissue in the cornea, sclera and other tissues, and are perhaps most well known for their impact on increasing intraocular pressure which can lead to glaucoma, optic nerve damage, cataracts or central serous chorioretinopathy (Fung 2020). Instillation related effects can include site related pain, burning or stinging, allergic reactions, foreign body sensation, visual disturbance, pruritus, urticaria, and rash; as well as keratitis, conjunctivitis, corneal ulcers, mydriasis, hyperemia, loss of accommodation, ptosis, acute anterior uveitis and perforation of the globe. (Pred Forte Label, 2017). Systemic side effects can include headache, elevated blood glucose and susceptibility to systemic microbial infections. In the eye, these side effects can occur even after even short-term (e.g., a few weeks) dosing. As such, corticosteroids make a suboptimal solution for inflammatory or immune-mediated ocular diseases, which often require mid or long-term anti-inflammatory management. Anti-histamines and cyclosporins are also frequently used for OSDs in large populations, to address allergic, immune-mediated, or inflammatory diseases of the eye, but these agents can also have profound side effects including irritation to eye tissue, cold symptoms, pharyngitis, and systemic side effects from delayed wound-healing to sulfite-related anaphylaxis. All of these commonly used immunomodulatory/immunosuppressive classes (including corticosteroids, anti-histamines, cyclosporins) can cause local side effects, particularly those of direct impact to patient quality of life (pain, discomfort, itching), which are exacerbated by the fact that these products are often given four to eight times a day or even more often, particularly at the beginning of their use, and often need to be tapered to lower doses because of these side effects. In clinical practice, it is not uncommon to use a corticosteroid every 1 to 2 hours for indications like anterior uveitis to attempt to get an adequate effect on the underlying inflammation inherent in this immune-mediated disease.

SUMMARY OF THE INVENTION

The present invention relates to methods of treating ocular inflammatory or immune-mediated diseases by administering ophthalmic pharmaceutical compositions of roflumilast. The inventors of the subject application have surprisingly discovered that administration of ophthalmic pharmaceutical compositions of roflumilast can provide clinically meaningful immunomodulatory and anti-inflammatory activity relative to existing standard of care therapies, including corticosteroids and antihistamines, while also providing an improved safety and convenience profile relative to one or both class of agents. The present invention addresses the high unmet need for an alternative class of agents to address the immune and inflammatory drivers of ocular surface and anterior/posterior ophthalmic disorders with clinically meaningful efficacy and yet lower patient-based or population-based side effects. With a strong efficacy and low level of side effects, the present invention can provide a short-term, mid-term, or long-term therapeutic solution for the many ocular diseases with an inflammatory or immune-mediated component.

An embodiment of the present invention provides for a method for treating a patient having an ocular inflammatory disorder. The method comprises administering an ophthalmic pharmaceutical suspension comprising a therapeutically effective amount of roflumilast or a pharmaceutically acceptable salt or metabolite thereof to an ocular surface of the patient. The administration results in a reduction of at least one side effect relative to administration of an immunosuppressant, immunomodulatory, or a non-steroidal anti-inflammatory agent. In certain embodiments, the administration of a roflumilast composition results in a reduction of at least one side effect relative to an ophthalmic prednisolone suspension or an anti-histamine olopatadine suspension.

In certain embodiments, the reduced side effect is an ocular side effect selected from the group consisting of: increase of intraocular pressure, thinning of corneal, scleral and epithelial tissue, perforation of corneal, scleral and epithelial tissue, delayed or decreased wound or epithelial healing, hyperemia, lid edema, pain, ocular pruritus, urticaria, rash, allergic reactions, keratitis, conjunctivitis, posterior subcapsular cataract formation, glaucoma, optic nerve damage, corneal ulcers, mydriasis, defects in vision, burning, stinging, foreign body sensation, increased susceptibility to fungal, bacterial, or viral infections, reactivation of fungal or viral infections, masking of acute purulent infections, increased bleb formation after surgery, dry eye, punctate keratopathy, central serous chorioretinopathy, and ophthalmicus medicamentosa, loss of accommodation, ptosis, acute anterior uveitis or perforation of the globe.

In certain embodiments, the reduced side effect is a systemic side effect selected from the group consisting of: change in blood glucose, weight gain or loss, decreased systemic wound healing, susceptibility to systemic microbial infections, irritation to tissues surrounding the eye, cold syndrome, pharyngitis, asthenia, back pain, headache, cough, nausea, rhinitis, sinusitis, osteoporosis, and taste perversion or dysgeusia, or sulfite-related anaphylaxis.

In certain embodiments, the administration downregulates cytokine or chemokine activity, particularly Th17, Th1, and/or Th2 cytokine activity, driven by inflammatory stress in at least one eye tissue selected from the group consisting of corneal and conjunctival tissue.

In certain embodiments, roflumilast more strongly downregulates cytokine activity, including Th1, Th2, and/or Th17 associated cytokines, relative to cytokine downregulation by immunosuppressant, immunomodulatory, or non-steroidal anti-inflammatory agents. Further, in certain embodiments, the downregulation of cytokines by roflumilast is more robust in the conjunctiva than by steroids or anti-histamines.

In certain embodiments, the administration results in disease-modifying activity in at least one supportive tissue or gland selected from the group consisting of the cornea, the conjunctiva, the Meibomian gland, the iris, the uvea, the retina, and the choroid.

In certain embodiments, the ocular inflammatory disorder is an ocular surface disease selected from the group consisting of: post-operative pain and inflammation from cataract or other ocular surgery or laser therapy, post-corneal refractive surgery haze, post-operative full or partial thickness corneal transplantation, dry eye syndrome associated with Sjogren's or other autoimmune or inflammatory disease, evaporative or desiccative dry eye disease, ocular graft vs host disease, ocular rosacea, allergic conjunctivitis or keratoconjunctivitis, atopic keratoconjunctivitis, vernal keratoconjunctivitis, keratitis, herpetic or viral keratitis including herpetic or viral stromal keratitis/herpetic or viral blepharitis or conjunctivitis, zoster related inflammation, inflammation secondary to other infectious agents such as bacterial, viral, or fungal infections, inflammation secondary to ocular chemical burns, ocular Stevens-Johnson syndrome/TENS, uveitis including uveitis of juvenile idiopathic arthritis, seborrheic or other forms of blepharitis, limbal stem cell deficiency, meibomian gland dysfunction, episcleritis, pingueculitis, and pterygia, phlyctenulosis, staphylococcal hypersensitivity, Mooren's ulcer, endotheleitis, superior limbic keratoconjunctivitis, or other ocular conditions traditionally treated with steroids where patients are contra-indicated due to a history of intra-ocular pressure, wound healing, or fungal or other microbial infections.

In certain embodiments, the ocular inflammatory disorder is an anterior or posterior ocular disease selected from the group consisting of: anterior-, pan- and posterior uveitis (infectious or non-infectious), diabetic retinopathy, diabetic macular edema, geographic atrophy, dry or wet age-related macular degeneration, retinal vein occlusion, drug related/iatrogenic, non-infectious/sterile, or idiopathic retinal vasculitis, endophthalmitis, or retinitis, ocular Bechet's disease, and other inflammatory diseases of the anterior and posterior tissues of the eye. In preferred embodiments, the ocular inflammatory disorder is dry eye disease, uveitis, or herpetic or viral keratitis.

Another embodiment of the present invention provides for a method for treating a patient having an ocular inflammatory or immune-mediated disorder. The method includes administering an ophthalmic pharmaceutical formulation comprising a therapeutically effective amount of roflumilast or a pharmaceutically acceptable salt or metabolite thereof to an ocular surface of the patient. The administration downregulates cytokine activity driven by inflammatory stress in at least one eye tissue selected from the group consisting of corneal and conjunctival tissue. In certain embodiments, the pharmaceutical formulation is a suspension.

Another embodiment of the present invention provides for a method for treating a patient having an ocular inflammatory or immune-mediated disorder. The method includes administering an ophthalmic pharmaceutical formulation comprising a therapeutically effective amount of roflumilast or a pharmaceutically acceptable salt or metabolite thereof to an ocular surface of the patient. The administration downregulates cytokine activity in a manner that is superior to the downregulation of cytokines by a corticosteroid or other immunosuppressant, immunomodulatory, or non-steroidal anti-inflammatory agent, including an antihistamine. In certain embodiments, the administration of a roflumilast composition results in the downregulation of cytokine activity in a manner that is superior to downregulation of cytokines by administration of an ophthalmic prednisolone suspension or an anti-histamine olopatadine suspension.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein. The error bars in the drawings are standard deviation values.

DETAILED DESCRIPTION OF THE INVENTION

Figure 1:
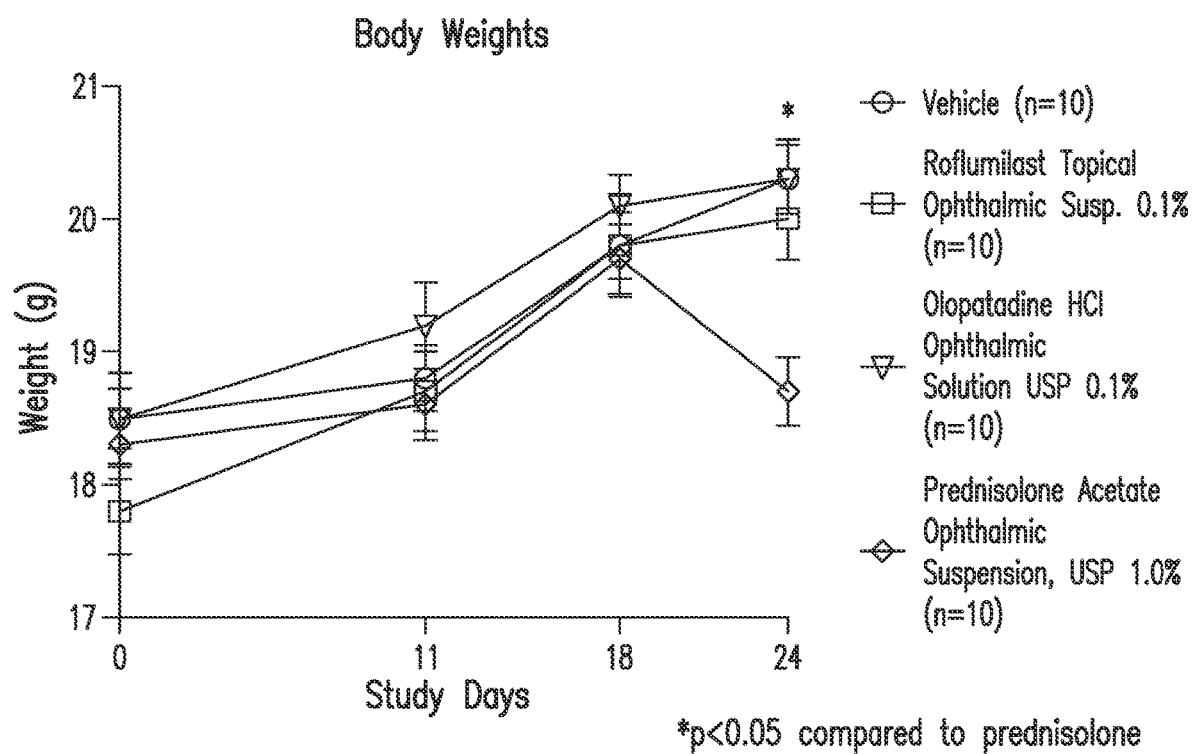
FIG. 1 provides data for the body weight following 7 days administration of roflumilast topical ophthalmic suspension (0.1%), vehicle, prednisolone acetate ophthalmic suspension (1.0%), and olopatadine HCl ophthalmic solution (0.1%) as measured in a murine preclinical model of systemic and topical allergen challenge.

It is to be understood that the invention is not limited to the particular methodology, protocols, and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients.

The term "about" when used in connection with a numerical value is meant to encompass numerical values within a range having a lower limit that is 5% smaller than the indicated numerical value and having an upper limit that is 5% larger than the indicated numerical value.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

The term "eye disorder," "eye condition," or "ocular disorder," refer to diseases/conditions of the eye(s) that can be sight threatening, lead to eye discomfort, and may signal systemic health problems. The eye surface is composed of the cornea, conjunctiva, eyelids, lacrimal and Meibomian glands, and the interconnecting nerves.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

The term "roflumilast" as used in this application refers to roflumilast, its salts, the N-oxide of roflumilast, and its salts and other hydrolytic or amide metabolites unless specified otherwise or unless it is clear in context that reference is to roflumilast itself.

As used herein, the terms "subject" or "patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The present invention relates to methods of treating ocular inflammatory diseases by administering ophthalmic pharmaceutical suspensions of roflumilast. The inventors of the subject application have surprisingly discovered that administration of ophthalmic pharmaceutical suspensions of roflumilast can provide clinically meaningful anti-inflammatory activity relative to existing immunomodulatory, immunosuppressive and non-steroidal anti-inflammatory therapies, including corticosteroids and antihistamines, while also providing an improved safety profile relative to these agents, and an added convenience benefit in the form of less frequent dosing. The present invention addresses the high unmet need for an alternative class of agents to address the inflammatory drivers of OSDs with high efficacy and yet lower patient-based or population-based side effects and inconveniences. The present invention can provide a short-term, mid-term, or long-term therapy for ocular diseases with an inflammatory or immune-mediated component.

In certain embodiments, the method comprises administering, to a patient suffering from an ocular inflammatory disease, an ophthalmic pharmaceutical suspension comprising a therapeutically effective amount of the phosphodiesterase-4 inhibitor, roflumilast or a pharmaceutically acceptable salt or metabolite thereof. In certain embodiments, the pharmaceutical composition comprises a metabolite of roflumilast, including the N-oxide of the pyridine residue of roflumilast or salts thereof, as an active ingredient.

Roflumilast is a compound of the formula (I):

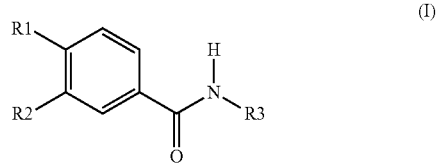

wherein R1 is difluoromethoxy, R2 is cyclopropylmethoxy and R3 is 3,5-dichloropyrid-4-yl.

Roflumilast has the chemical name N-(3,5-dichloropyrid-4-yl)-3-cyclopropylmethoxy-4-difluoromethoxybenzamide. The N-oxide of roflumilast has the chemical name 3-cyclopropylmethoxy-4-difluoromethoxy-N-(3,5-dichloropyrid-4-yl 1-oxide)benzamide. Roflumilast and its synthesis, the use of roflumilast as a phosphodiesterase (PDE) 4 inhibitor, and roflumilast formulations, were described in U.S. Pat. No. 5,712,298, which is incorporated herein by reference. The ophthalmic pharmaceutical composition can include roflumilast as a free base or a pharmaceutically acceptable salt. Exemplary salts of roflumilast are salt described in paragraphs [0012] and [0013] of U.S. Patent Application Publication No. US 2006/0084684, the disclosure of which is incorporated herein by reference. In certain embodiments, the pharmaceutical composition comprises a metabolite of roflumilast, including the N-oxide of the pyridine residue of roflumilast or salts thereof, as an active ingredient. In certain embodiments, the pharmaceutical composition comprises a hydrolytic or amide metabolite of roflumilast.

In certain embodiments of the present invention, roflumilast is administered to an ocular surface of a patient having an eye disorder or eye condition, including for example an ocular inflammatory disorder. In certain embodiments, the ocular inflammatory disorder is an ocular surface disease selected from the group consisting of: post-operative pain and inflammation from cataract or other ocular surgery or laser therapy, post-corneal refractive surgery haze, post-operative full or partial thickness corneal transplantation, dry eye syndrome associated with Sjogren's or other autoimmune or inflammatory disease, evaporative or desiccative dry eye disease, ocular graft vs host disease, ocular rosacea, allergic conjunctivitis or keratoconjunctivitis, atopic keratoconjunctivitis, vernal keratoconjunctivitis, keratitis, herpetic or viral keratitis including herpetic or viral stromal keratitis/herpetic or viral blepharitis or conjunctivitis, zoster related inflammation, inflammation secondary to other infectious agents such as bacterial, viral, or fungal infections, inflammation secondary to ocular chemical burns, ocular Stevens-Johnson syndrome/TENS, uveitis including uveitis of juvenile idiopathic arthritis, seborrheic or other forms of blepharitis, limbal stem cell deficiency, meibomian gland dysfunction, episcleritis, pingueculitis, and pterygia, phlyctenulosis, staphylococcal hypersensitivity, Mooren's ulcer, endotheleitis, superior limbic keratoconjunctivitis, or other ocular conditions traditionally treated with steroids where patients are contra-indicated due to a history of intra-ocular pressure, wound healing, or fungal or other microbial infections.

In certain embodiments of the present invention, roflumilast is administered to an anterior or posterior segment of the eye of a patient having an eye disorder or eye condition. In certain embodiments, the ocular inflammatory disorder is an anterior or posterior ocular disease selected from the group consisting of: anterior-, pan-, and posterior uveitis (infectious or non-infectious), diabetic retinopathy, diabetic macular edema, geographic atrophy, dry or wet age-related macular degeneration, retinal vein occlusion, drug related/iatrogenic, non-infectious/sterile, or idiopathic retinal vasculitis, endophthalmitis, or retinitis, ocular Bechet's disease, and other inflammatory diseases of the anterior and posterior tissues of the eye. In preferred embodiments, the ocular inflammatory disorder is dry eye disease, uveitis, or herpetic or viral keratitis.

Other examples of eye disorders that can be treated by the methods disclosed herein can include ocular conditions traditionally treated with corticosteroids where patients are contra-indicated due to a history of intraocular pressure, wound healing, fungal or other microbial infections, thin or punctate corneal or retinal epithelial tissue etc., or intolerance or inability to comply with the frequency of administration or intolerance to the medication itself. The eye disorders treatable by the methods described herein can be acute or chronic. In certain embodiments, the eye disorder originates from an infectious or other external antigen origin but which then creates an inflammatory cascade. In preferred embodiments, the ocular inflammatory disorder is dry eye disease, uveitis or herpetic or viral stromal keratitis.

In certain embodiments, an ophthalmic pharmaceutical formulation is administered as an injection of multiple types (including intravitreal, suprachoroidal, sub-tenon, subconjunctival or other site) or a device, implant, or depot which can be used to treat anterior or posterior inflammatory ocular disease such as anterior, pan- and/or posterior uveitis (infectious or non-infectious), diabetic retinopathy, diabetic macular edema, geographic atrophy, dry or wet age related macular degeneration, retinal vein occlusion, drug related/iatrogenic, non-infectious/sterile, or idiopathic retinal vasculitis, endophthalmitis, or retinitis, ocular manifestations of Bechet's disease, or other inflammatory diseases of the anterior and posterior tissues of the eye.

In certain embodiments, the pharmaceutical composition is administered as a regimen, such as at regular intervals. For example, a pharmaceutical composition can be administered directly to the ocular surface once daily, twice daily, thrice daily, four times daily, once per week, twice per week, three times per week, or four times per week, monthly, as needed (PRN) or treat and extend. In certain embodiments, the pharmaceutical composition can be administered as part of a maintenance dose or titrating dose regimen. The pharmaceutical composition can be administered for a prescribed period of time. For example, a pharmaceutical composition can be administered for a period of about two days to at least about six weeks, or until an improvement in the eye condition or disease is observed. Exemplary periods of time for the treatment regimen include one week, two weeks, one month, six weeks, two months, three months, four months, five months, six months, seven months, eight months, nine months, or one year. For example a pharmaceutical composition can be administered as an injection or as a implantable device, depot, or adsorbable device could be administered once per week, once per month, once every 2, 3, 4, 5, 6, 7, 8, 9, 10, 11, 12, 13, 14, 15, 16 weeks, once per quarter, once every sixth months, as needed (PRN), per physician direction, or per some clinical criteria such as treat and extend or other criteria. The pharmaceutical composition can be administered as an ongoing treatment with no end.

In certain embodiments, administration of the ophthalmic pharmaceutical composition of roflumilast to a patient results in significant immunomodulatory and anti-inflammatory activity. The anti-inflammatory activity achieved as a result of the methods disclosed herein can be similar to, equal to, or greater than anti-inflammatory activity achieved via frequently dosed, commonly used, and potent corticosteroids and/or antihistamines, including but not limited to ophthalmic prednisolone suspensions and ophthalmic olopatadine solutions. Roflumilast as a PDE4 inhibitor is known to have a broad spectrum inhibitory impact on inflammatory mediators such as cytokines via an increase in cyclic AMP and other downstream mediators. The methods disclosed herein can downregulate cytokine disease activity driven by inflammatory stress in both conjunctival and corneal tissues, particularly Th17, Th1, and Th2 cytokines. Further, the methods disclosed herein can extend disease-modifying activity beyond conjunctival and corneal tissue to supportive tissues such as the Meibomian glands and other eye and orbital tissues, including anterior tissues such as the iris (including ciliary bodies) and uvea, and posterior tissues such as the retina and choroid. The methods of the present invention can result in reduction of inflammatory activity as well as decreased trafficking of cytokines and immune cells across cellular tissue as evidenced by the reduction of signs of inflammation and/or trafficking of cytokines in and across the cornea and conjunctiva. The down-regulation of cytokines and chemokines is also important for the reduction of chemotaxis of blood vessels or neovascular growth, macrophage polarization, and broader infiltrating t- and b-cell immune responses across ocular tissue and in exchanges between the eye and the broader systemic environment. In certain embodiments, the down regulation of the cytokine activity and related immune activity by roflumilast is similar to or superior to immunomodulatory and immunosuppressive agents such as corticosteroids or antihistamines.

Additionally, the safety profile of the methods disclosed herein can be similar to, equal to or better than the safety profile of frequently dosed, commonly used, and potent corticosteroids and/or anti-histamines, including but not limited to ophthalmic prednisolone suspensions and ophthalmic olopatadine solutions. In certain embodiments, the methods result in a reduction of at least one side effect relative to administration of an ophthalmic prednisolone suspension or other corticosteroid. In certain embodiments, the reduced side effect is an ocular side effect selected from the group consisting of: increase of intraocular pressure, thinning of corneal, scleral and epithelial tissue, perforation of corneal, scleral and epithelial tissue, delayed or decreased wound or epithelial healing, hyperemia, lid edema, pain, ocular pruritus, urticaria, rash, allergic reactions, keratitis, conjunctivitis, posterior subcapsular cataract formation, glaucoma, optic nerve damage, corneal ulcers, mydriasis, defects in vision, burning, stinging, foreign body sensation, increased susceptibility to fungal, bacterial, or viral infections, reactivation of fungal or viral infections, masking of acute purulent infections, increased bleb formation after surgery, dry eye, punctate keratopathy, central serous chorioretinopathy, and ophthalmicus medicamentosa, loss of accommodation, ptosis, acute anterior uveitis and perforation of the globe.

In certain embodiments, the reduced side effect is a systemic side effect selected from the group consisting of: changes in blood glucose, weight gain or loss, decreased systemic wound healing, susceptibility to systemic microbial infections, irritation to tissues surrounding the eye, cold syndrome, pharyngitis, asthenia, back pain, headache, cough, nausea, rhinitis, sinusitis, osteoporosis, and taste perversion or dysgeusia, and sulfite-related anaphylaxis. Additionally, inactive ingredients and preservatives in these pharmaceutical ingredients can be absorbed into contact lenses of contact lens wearers.

Additionally, in certain embodiments, the use of a roflumilast pharmaceutical composition can provide the patient and caregiver benefit of less frequent administration which is both more convenient, allowing patients to work, travel, and leave the house without their medications, but also can mean avoidance of pain and discomfort of drug application many times per day. The PK profile of the agent is such that it can be used in certain embodiments once or twice per day (QD or BID) was compared to frequent dosing of QID, eight times per day or more for corticosteroids. In some ocular diseases, physicians ask their patients to use a corticosteroid topical ophthalmic preparation once every one or two hours and wake during the night to instill additional doses, causing significant patient and caregiver burden.

Additionally, for patients with moderate to long-term requirements for anti-inflammatory pharmaceutical intervention, the use of corticosteroids comes with an increased patient and physician practice burden, as the patient will require frequent monitoring for safety concerns including intra-ocular pressure, cataract formation, and infection. This is particularly difficult in patients where this monitoring is challenging or uncomfortable: young children, elderly, patients with ocular tissue which is sensitive due to long-term disease, all of which groups have frequent overlap with inflammatory ocular disease. In the current embodiment, this agent could avoid the need and cost for such frequent monitoring.

In the present invention, a patient in need thereof is administered an ophthalmic pharmaceutical composition comprising a therapeutically effective amount of roflumilast. The ophthalmic pharmaceutical composition can be formulated into such preparations utilizing a number of well-known and widely used methods to those of ordinary skill in the art. For example, the ophthalmic pharmaceutical composition can be a gel, ointment, cream, solution, suspension, or other topical formulation. In certain embodiments, the ophthalmic pharmaceutical composition can be a periocular or subconjunctival implant or injection via various sites (intravitreal, subconjunctival, sub-tenon, suprachoroidal, or others), or an intracorneal or intravitreal implant, injection, or depot. In preferred embodiments, the ophthalmic pharmaceutical composition is administered topically, directly to the eye, in the form of a suspension.

In certain embodiments, the ophthalmic pharmaceutical composition can comprise roflumilast in a range from about 0.01% w/v to about 5.0% w/v, or from about 0.01% w/v to about 3.0% w/v, or from about 0.01% w/v to about 2.0% w/v, or from about 0.01% to about 1.0% w/v, or from about 0.01% to about 0.3% w/v. For example, the ophthalmic pharmaceutical comprises any of the following w/v percents of roflumilast: 0.01,%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the ophthalmic pharmaceutical composition can be a suspension, solution eye drops, eye ointments, gels, creams, a spray, a nasal spray, an injectable formulation (intravitreal, subconjunctival, sub-tenon, suprachoroidal or other injections), or an adsorbent device or implant or depot, or adsorbent contact lens. In preferred embodiments, the pharmaceutical composition is a suspension, wherein the active ingredient (i.e., roflumilast) is suspended in a pharmaceutical carrier and/or excipients. In certain embodiments, the ophthalmic pharmaceutical composition of roflumilast comprises a viscosity agent, a surfactant, and a buffer. In certain embodiments, the ophthalmic pharmaceutical composition can include one or more additional excipients, including for example, a stabilizer, a preservative, a wetting agent, a diluting agent, a pH adjuster, a tonicity agent, or an absorption enhancer. In certain embodiments, the ophthalmic pharmaceutical composition can also be utilized for anterior or posterior ophthalmic situations in the form of an injection (intravitreal, suprachoroidal, or other), as a depot, an implantable adsorbent device for any ophthalmic or surrounding tissue placement, an in situ forming gel, or a drug/device combination, wherein the active ingredient (i.e., roflumilast) is suspended with one or more of the excipients above, for example a viscosity agent, a surfactant, or a buffer; with or without a device or inert depot compound.

In certain embodiments, the viscosity agent is at least one selected from the group consisting of hydroxypropyl methylcellulose (HPMC), hydroxyethylcellulose (HEC), polyvinyl pyrrolidione or povidone, carboxymethyl cellulose, hypromellose, methylcellulose, or polyvinyl alcohol (PVA). In certain embodiments, the viscosity agent is a dextran or gelatin. In addition, the viscosity agent can include a carbomer in certain embodiments, such as a carbomer copolymer Type A or a carbomer copolymer Type B including those marketed under the trade name Carbopol® by Lubrizol®. In certain embodiments, the ophthalmic pharmaceutical formulation can comprise a viscosity agent in a range from about 0.1% w/v to about 5.0% w/v, or from about 0.1% w/v to about 4.0% w/v, or from about 0.1% w/v to about 3.0% w/v, or from about 0.1% w/v to about 2.0% w/v, or from about 0.1% to about 1.0% w/v, or from about 0.1% to about 0.5% w/v. For example, the ophthalmic pharmaceutical comprises any of the following w/v percents of a viscosity agent: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the surfactant is at least one selected from the group consisting of polysorbates (including, polysorbate 20, polysorbate 40, polysorbate 60, and polysorbate 80) and tyloxapol. In certain embodiments, the ophthalmic pharmaceutical formulation can comprise a surfactant in a range from about 0.05% w/v to about 3.0% w/v, or from about 0.05% w/v to about 2.0% w/v, or from about 0.05% to about 1.0% w/v, or from about 0.1% to about 0.5% w/v. For example, the ophthalmic pharmaceutical comprises any of the following w/v percents of a surfactant: 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the buffer is at least one selected from the group consisting of citrate, phosphate, Tris-HCl (Tris), acetate, and borate buffers. In certain embodiments, the ophthalmic pharmaceutical formulation can comprise a buffer in a range from about 0.5% w/v to about 7.5% w/v, or from about 0.5% w/v to about 5.0% w/v, or from about 0.5% to about 3.0% w/v, or from about 0.5% w/v to about 2.0% w/v, or from about 0.5% to about 1.0% w/v. For example, the ophthalmic pharmaceutical comprises any of the following w/v percents of a buffer: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the ophthalmic pharmaceutical formulation is an ointment. The ointment can include inactive ingredients selected from the group consisting of petrolatum, mineral oil, In such embodiments, the ophthalmic pharmaceutical formulation can comprise a therapeutically effective amount of roflumilast, petrolatum, and mineral oil. In certain embodiments, the composition comprises from about 0.1% w/v to about 3.0% w/v, or from about 0.1% w/v to about 2.0% w/v, or from about 0.1% w/v to about 1.0% w/v of roflumilast. In certain embodiments, the composition comprises from about 75% to about 85% w/w of petrolatum, or more preferably from about 75% to about 80% w/w of petrolatum. In certain embodiments, the composition comprises from about 15% to about 25% w/w mineral oil, or more preferably from about 15% to about 20% w/w of mineral oil. The ointment can provide benefits relative to suspensions, including for example, increasing contact time and increasing the soluble drug concentration in the dosing system, which can be important for a water-insoluble drug like roflumilast.

The inventors of the subject application have identified that roflumilast undergoes hydrolysis in certain ophthalmic pharmaceutical compositions and under certain standard sterile manufacturing processes. In certain embodiments, the pH of the ophthalmic pharmaceutical composition is between 5.5 and 7.5 In preferred embodiments, the pH of the ophthalmic pharmaceutical compositions is between about 6.0 and about 6.7 to reduce the rate of hydrolysis of roflumilast. In certain embodiments, the pH of the ophthalmic pharmaceutical composition is between about 6.2 and about 6.7, or in some embodiments, between 6.3 and 6.6. In certain embodiments, the osmolality of the ophthalmic pharmaceutical composition is about 270 mOsm/kg to 330 mOsm/kg, more preferably about 270 mOsm/kg to about 300 mOsm/kg, and even more preferably 270 mOsm/kg to 280 mOsm/kg.

The ophthalmic pharmaceutical compositions of the present invention are stable and exhibit a particle size distribution suitable for ophthalmic delivery. Particle size of the ophthalmic pharmaceutical composition for suspensions can be assessed using laser diffraction methods. Laser diffraction is recognized by standards and guidance agencies including ISO and ASTM and is widely used to determine particle size distributions. In conducting the assessment, the sample is passed through a laser beam, which results in laser light scattered at a range of angles. Detectors placed at fixed angles measure the intensity of light scattered at that position. A mathematical model is then applied to generate a particle size distribution.

In particle size determinations, the median value is defined as the value where half of the population resides above this point, and half resides below this point. For particle size distributions the median is called the D50. The D50 is the size that splits the distribution with half above and half below this diameter. The distribution width may also be characterized by citing one, two or three values on the x-axis, typically some combination of the D10, D50, and D90. The D50 (or the median), as discussed above, refers to the diameter wherein half of the population lies below this value. Similarly, 90 percent of the distribution lies below the D90, and 10 percent of the population lies below the D10.

In certain embodiments of the present invention, the ophthalmic pharmaceutical composition exhibits a particle size distribution characterized by a d90 value of less than or equal to about 50 μm prior to preferential processing. In certain embodiments, the ophthalmic pharmaceutical composition exhibits a particle size distribution characterized by a d90 value of from about 5 μm to about 25 μm. In certain embodiments, the pharmaceutical compositions exhibits a particle size distribution characterized by a d90 value of from about 5 μm to about 15 μm. In preferred embodiments, the pharmaceutical compositions exhibit a particle size distribution characterized by a d90 value of less than or equal to 10 μm.

In certain embodiments, the pharmaceutical composition of roflumilast is sterilized using slow dry heat sterilization at a temperature less than the melting point of roflumilast, gamma radiation, or other methods of sterilization. In certain embodiments, gamma radiation or other terminal product sterilization methods can be used to sterilize the final drug product in its terminal packaging by application of low-moderate level gamma radiation to ensure sterility, which is a preferred embodiment for maximum patient safety and comfort, as the product will not need to contain preservatives which are known to sting upon application. In certain embodiments, the ophthalmic pharmaceutical composition can be characterized by a retained potency of greater than 99% of the original value of active substances. In certain embodiments, the retained potency is greater than 99.1%, 99.2%, 99.3%, 99.4%, or 99.5% of the original value of active substances.

The following examples illustrate certain embodiments of the invention without limitation.

EXAMPLES

While various embodiments have been described herein, it should be understood that they have been presented by way of example only, and not limitation. Thus, the breadth and scope of the present disclosure should not be limited by any of the described exemplary embodiments. Moreover, any combination of the above-described elements in all possible variations thereof is encompassed by the disclosure unless otherwise indicated herein or otherwise clearly contradicted by context.

Example 1

The ophthalmic pharmaceutical compositions comprising roflumilast set forth in Table 1 were prepared.

TABLE 1

Ophthalmic Pharmaceutical Suspensions of Roflumilast

| Ingredient | 0.1% Roflumilast HPMC Suspension | 0.3% Roflumilast HPMC Suspension | 1.0% Roflumilast HPMC Suspension | 3.0% Roflumilast HPMC Suspension |
|---|---|---|---|---|
| Roflumilast | 0.1% w/w | 0.3% w/w | 1.0% w/w | 3.0% w/w |
| Hypromellose (HPMC) | 0.3% | 0.3% | 0.3% | 0.3% |
| Polysorbate 80 | 0.1% | 0.1% | 0.1% | 0.1% |
| Sodium phosphate dibasic heptahydrate | 0.25% | 0.25% | 0.25% | 0.25% |
| Citric acid monohydrate | 0.05% | 0.05% | 0.05% | 0.05% |
| Sodium chloride | 0.7% | 0.7% | 0.7% | 0.7% |
| 1N HCl and/or 1N NaOH | Adjust pH to 6.5 | Adjust pH to 6.5 | Adjust pH to 6.5 | Adjust pH to 6.5 |
| Purified Water | q.s. to 100% | q.s. to 100% | q.s. to 100% | q.s. to 100% |

Example 2

The ophthalmic pharmaceutical compositions comprising roflumilast set forth in Table 2 was prepared.

TABLE 2

Ophthalmic Pharmaceutical Suspension of Roflumilast

| Ingredient | % w/v |
|---|---|
| Roflumilast | 0.1% w/v |
| Hydroxyethyl cellulose | 0.35% w/v |
| Polysorbate 80 | 0.1% w/v |
| Phosphate/Citrate Buffer | 0.45%/0.05% |
| Water for injection | q.s. ad 1.0 mL |

Example 3

The ophthalmic pharmaceutical compositions comprising roflumilast set forth in Table 3 were prepared.

TABLE 3

Ophthalmic Pharmaceutical Suspensions of Roflumilast

| Ingredient | 0.1% Roflumilast PVP Suspension | 0.3% Roflumilast PVP Suspension | 1.0% Roflumilast PVP Suspension | 3.0% Roflumilast PVP Suspension |
|---|---|---|---|---|
| Roflumilast | 0.1% w/w | 0.3% w/w | 1.0% w/w | 3.0% w/w |
| Povidone (K30) PVP | 0.6% | 0.6% | 0.6% | 0.6% |

TABLE 3-continued

Ophthalmic Pharmaceutical Suspensions of Roflumilast

| Ingredient | 0.1% Roflumilast PVP Suspension | 0.3% Roflumilast PVP Suspension | 1.0% Roflumilast PVP Suspension | 3.0% Roflumilast PVP Suspension |
|---|---|---|---|---|
| Tyloxapol | 0.3% | 0.3% | 0.3% | 0.3% |
| Sodium phosphate dibasic heptahydrate | 0.25% | 0.25% | 0.25% | 0.25% |
| Citric acid monohydrate | 0.05% | 0.05% | 0.05% | 0.05% |
| Sodium chloride | 0.7% | 0.7% | 0.7% | 0.7% |
| 1N HCl and/or 1N NaOH | Adjust pH to 6.5 | Adjust pH to 6.5 | Adjust pH to 6.5 | Adjust pH to 6.5 |
| Purified Water | q.s. to 100% | q.s. to 100% | q.s. to 100% | q.s. to 100% |

Example 4

The ophthalmic pharmaceutical composition comprising roflumilast set forth in Table 4 was prepared.

TABLE 4

Ophthalmic Pharmaceutical Suspension of Roflumilast

| Ingredient | % w/v |
|---|---|
| Roflumilast | 0.1% w/v |
| Carboxymethyl cellulose | 0.5% w/v |
| Polysorbate 80 | 0.1% w/v |
| Phosphate/Citrate Buffer | 0.45%/0.05% |
| Water for injection | q.s. ad 1.0 mL |

Examples 5 and 6

The ophthalmic pharmaceutical ointments comprising roflumilast set forth in Table 5 was prepared.

TABLE 5

Ophthalmic Pharmaceutical Ointments of Roflumilast

| Ingredient | Example 5 (% w/w) | Example 6 (% w/w) |
|---|---|---|
| Roflumilast | 0.1% w/w | 1% w/w |
| Mineral oil | 20.2% w/w | 20% w/w |
| Petrolatum | 79.7% w/w | 79% w/w |

Example 7

An ophthalmic pharmaceutical compositions comprising roflumilast as set forth in Table 6 was prepared.

TABLE 6

Ophthalmic Pharmaceutical Suspension of Roflumilast at 0.1% w/v

| Excipient | Concentration (mg/mL) |
|---|---|
| Roflumilast | 1.0 |
| Carbopol 974B (Lubrizol) | 2.5 |
| Tyloxapol | 0.5 |
| Sodium chloride | 3.0 |
| Mannitol | 3.0 |
| Propylene Glycol | 14.0 |
| NaOH/HCl | As needed to adjust pH to 7.4 |

Example 8

Two animal studies were conducted to assess the safety and tolerability of roflumilast (Example 7). Roflumilast was shown to be well tolerated in the two animal models, which are highly correlated to human models. The first study was a 3-day pilot of rabbit tolerability, the second was a 5-day rabbit model of tolerability, which found limited to no impact of the drug on ocular tissue as well as no adverse effect on animal weight. Animals in these studies maintained body weight or gained a normal amount of body weight over the study periods. Rabbit ocular tolerability is a well-known surrogate for human tolerability for ophthalmic preparations, and body weight a measure of overall health of the animal.

Example 9

The safety of roflumilast (Example 7, BID) was compared to the safety of corticosteroids (prednisolone acetate ophthalmic suspension, 1%, QID to BID) and antihistamines (olopatadine HCl ophthalmic solution, 0.1%, QID to BID) in a 24-day murine preclinical model of allergic conjunctivitis with long-term inflammation. In a murine preclinical model of short-term and long-term inflammation brought on by antigen challenge with a systemic and topical ragweed allergen (SRW), n=70 female Balb C mice in a challenged environment (68-79dF, 50%+/−20% humidity, 55-60 air changes/hr), were exposed systemically to a SRW by SC injections in both hind legs at day 0 and 11 over the course of 17 days. Next, they were exposed to a topical SRW challenge at day 18 (first topical challenge-baseline) followed by first topical drug treatment of roflumilast (Example 7), vehicle without active drug, frequent dose (BID-QID) high dose prednisolone 1%, or frequent dose (BID-QID) olopatadine 0.1%. Mice were randomized at day 18 (10 per arm) based on achieving a clinical level of hyperemia response. Mice were then given two days (days 19-20) of prophylactic drug treatment and then tracked for their response to drug treatment (BID for Roflumilast Topical Ophthalmic Suspension and Vehicle), QID, TID, or BID for the two positive controls (prednisolone and olopatadine)) prior to an SRW antigen topical challenge twice per day (within 30-90 minutes of drug treatment) for days 21-24. Results of this study are set forth in FIGS. 1-5 and described below. Murine models are commonly used to compare standard of care corticosteroids and anti-histamines to novel agents.

Figure 2:
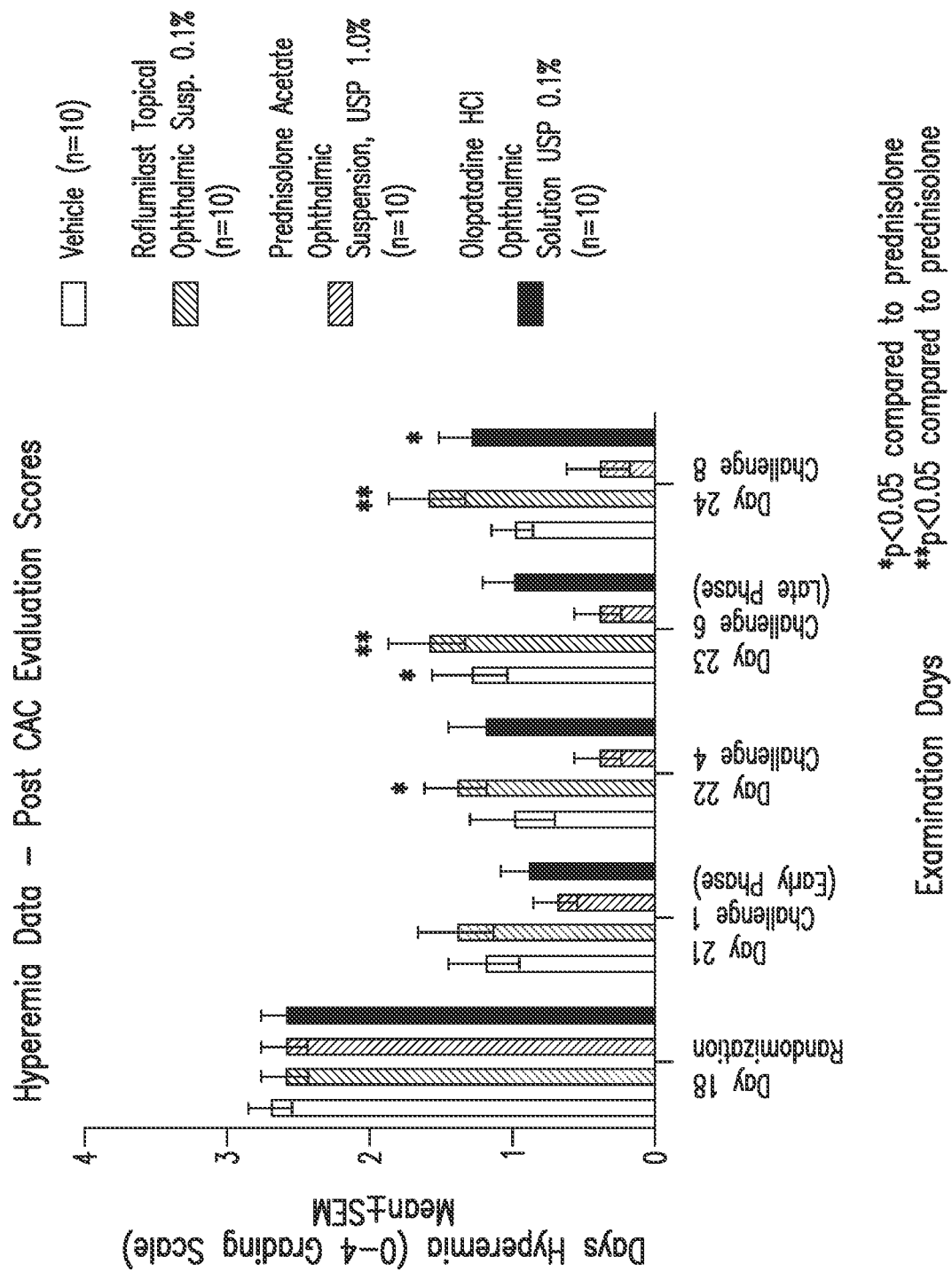
FIG. 2 provides data for the clinical response of hyperemia following administration of roflumilast topical ophthalmic suspension (0.1%), vehicle, prednisolone acetate ophthalmic suspension (1.0%), and olopatadine HCl ophthalmic solution (0.1%) as measured in a murine preclinical model of systemic and topical allergen challenge FIG. 3 provides data for the clinical response of lid swelling following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.
Figure 3:
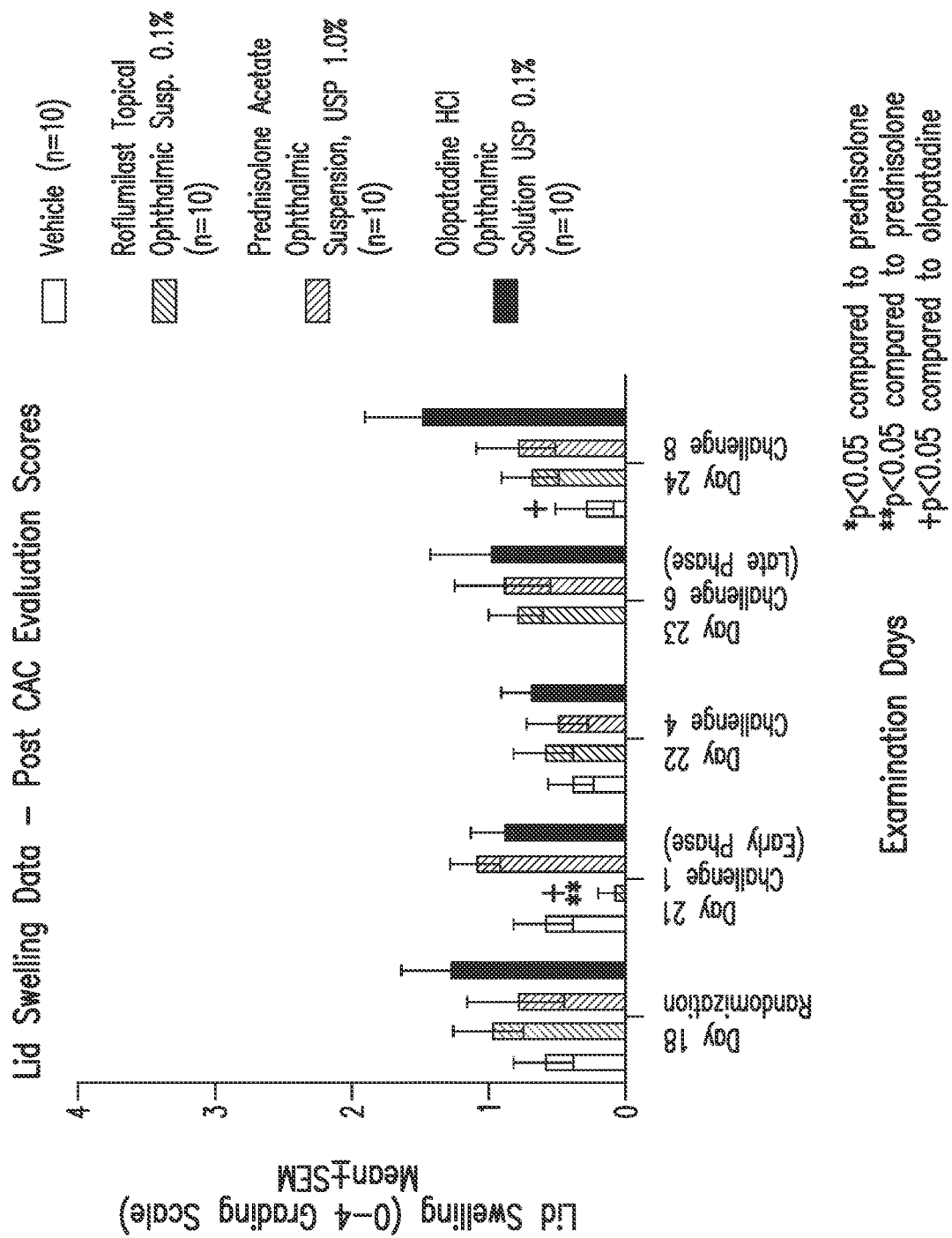
Figure 4:
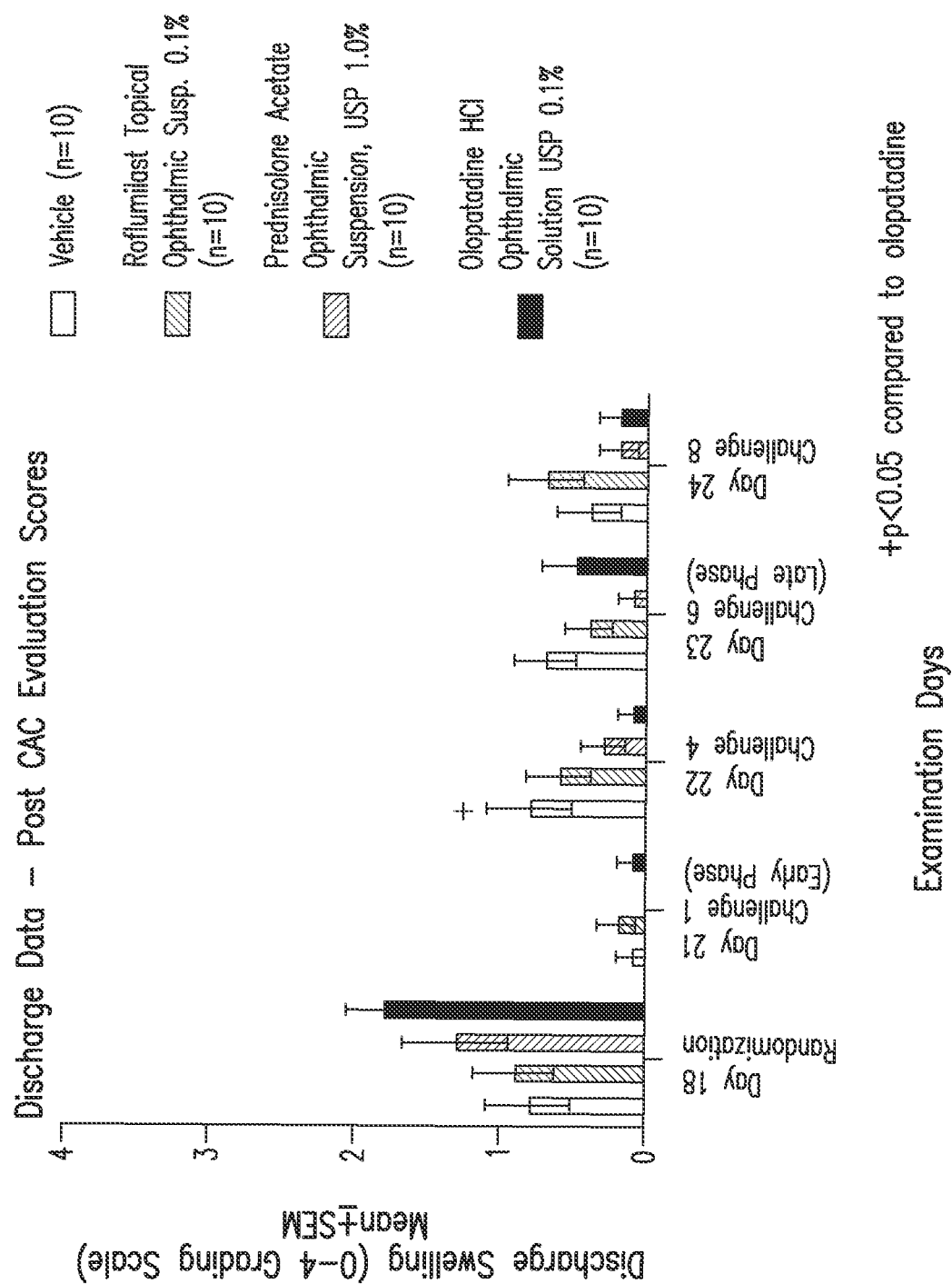
FIG. 4 provides data for the clinical response of discharge following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.
Figure 5:
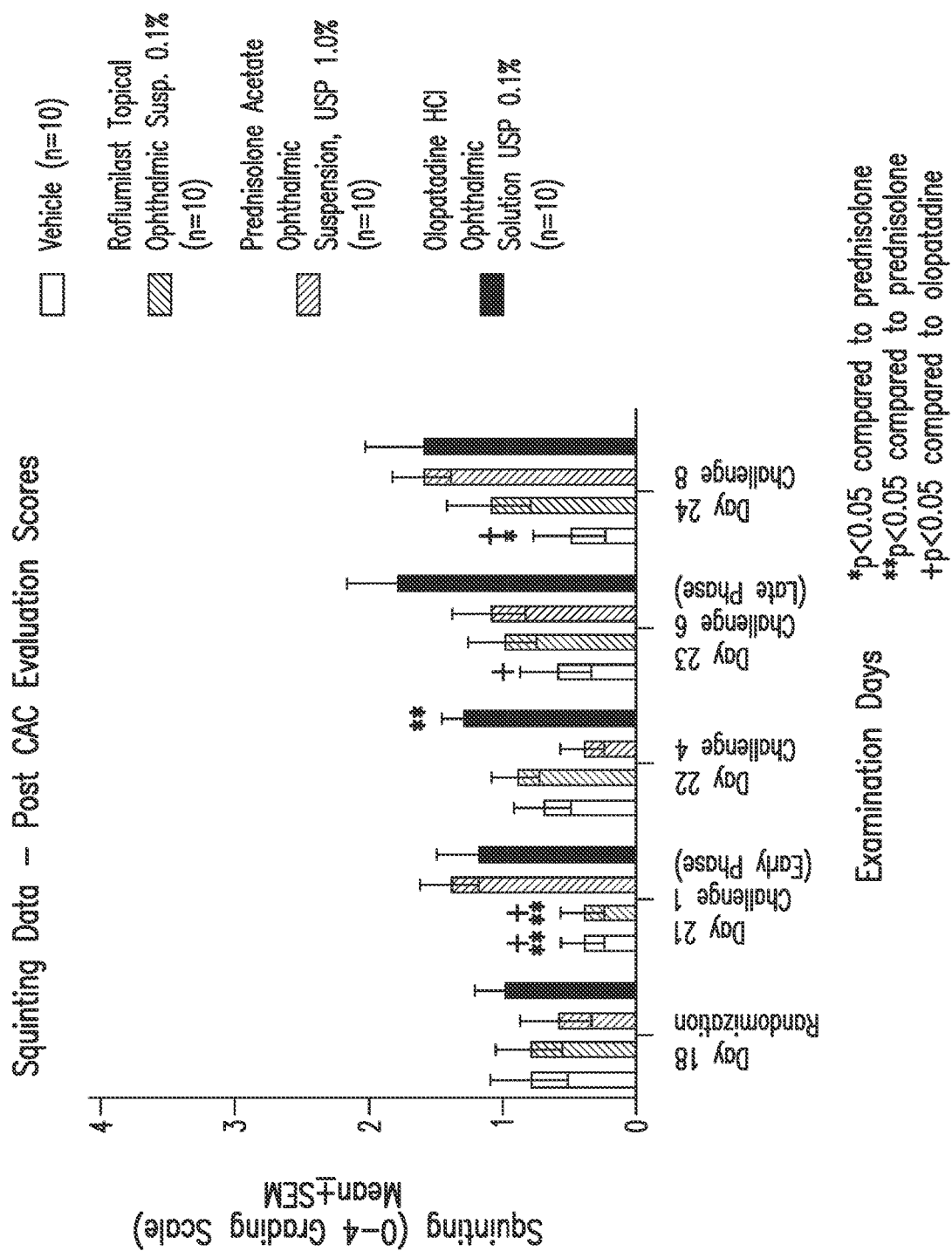
FIG. 5 provides data for the clinical response of squinting following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.

Drug dosing only began on day 18. During the study, the body weight of the mice was determined after days 11, 18, and 24 of the study. FIG. 1 illustrates the body weight of mice following administration of roflumilast topical ophthalmic suspension (0.1%), vehicle, prednisolone acetate ophthalmic suspension (1.0%), and olopatadine HCl ophthalmic solution (0.1%) as measured in an animal model study. The mice exposed to the high-frequency, high-dose corticosteroids showed a weight decrease over the course of days 18-24, which is a typical response to mice exposed to corticosteroids. Although different than human response, is a sign of overall systemic health risk due to even topical corticosteroid exposure. In the roflumilast arm, no impact on body weight, cageside observations, food consumption, or other markers of overall ocular or systemic health were found, which suggest the agent is well tolerated. The inflammatory clinical responses of hyperemia, lid swelling, discharge and squinting were also examined at days 18, 21 (early stage), and 22, 23, and 24 (late stage). FIG. 2 illustrates the clinical response of hyperemia following administration of roflumilast topical ophthalmic suspension (0.1%), vehicle, prednisolone acetate ophthalmic suspension (1.0%), and olopatadine HCl ophthalmic solution (0.1%) as measured in an animal model study. FIG. 3 illustrates the clinical response of lid swelling following administration of roflumilast topical ophthalmic suspension (0.1%), vehicle, prednisolone acetate ophthalmic suspension (1.0%), and olopatadine HCl ophthalmic solution (0.1%) as measured in an animal model study. FIG. 4 illustrates the clinical response of discharge following administration of roflumilast topical ophthalmic suspension (0.1%), vehicle, prednisolone acetate ophthalmic suspension (1.0%), and olopatadine HCl ophthalmic solution (0.1%) as measured in an animal model study. FIG. 5 illustrates the clinical response of squinting following administration of roflumilast topical ophthalmic suspension (0.1%), vehicle, prednisolone acetate ophthalmic suspension (1.0%), and olopatadine HCl ophthalmic solution (0.1%) as measured in an animal model study.

As illustrated in FIG. 5, both the corticosteroid and antihistamine arms showed an increase in squinting across the course of the study, which can also be perceived as a marker for topical irritation. Squinting was lesser in both the roflumilast and vehicle arms, significantly so in the early phase. No cageside safety or behavior issues were seen for any of the arms outside of the aforementioned weight loss and squinting. As such, the roflumilast and vehicle arms showed improved tolerability in this preclinical study relative to the active controls, which represent the present standard of care in human medicinal topical treatment of most OSDs.

Further, as illustrated in FIGS. 2-5, the preclinical murine model of long-term inflammation caused by both a systemic and topical model of allergic conjunctivitis illustrated that roflumilast was able to improve inflammatory clinical responses of hyperemia, lid swelling, discharge and squinting compared to baseline. Significance from baseline was not measured in this experiment. Although the overall baseline inflammation seen in this model was relatively low, the therapeutic interventions generally performed better than baseline and provided clinical improvements, including the roflumilast arm. The corticosteroid arm performed better than the other arms in a small number of days and clinical endpoints, but not consistently, suggesting that roflumilast can provide a similar level of efficacy without the safety concerns outlined above.

Example 10

Figure 6:
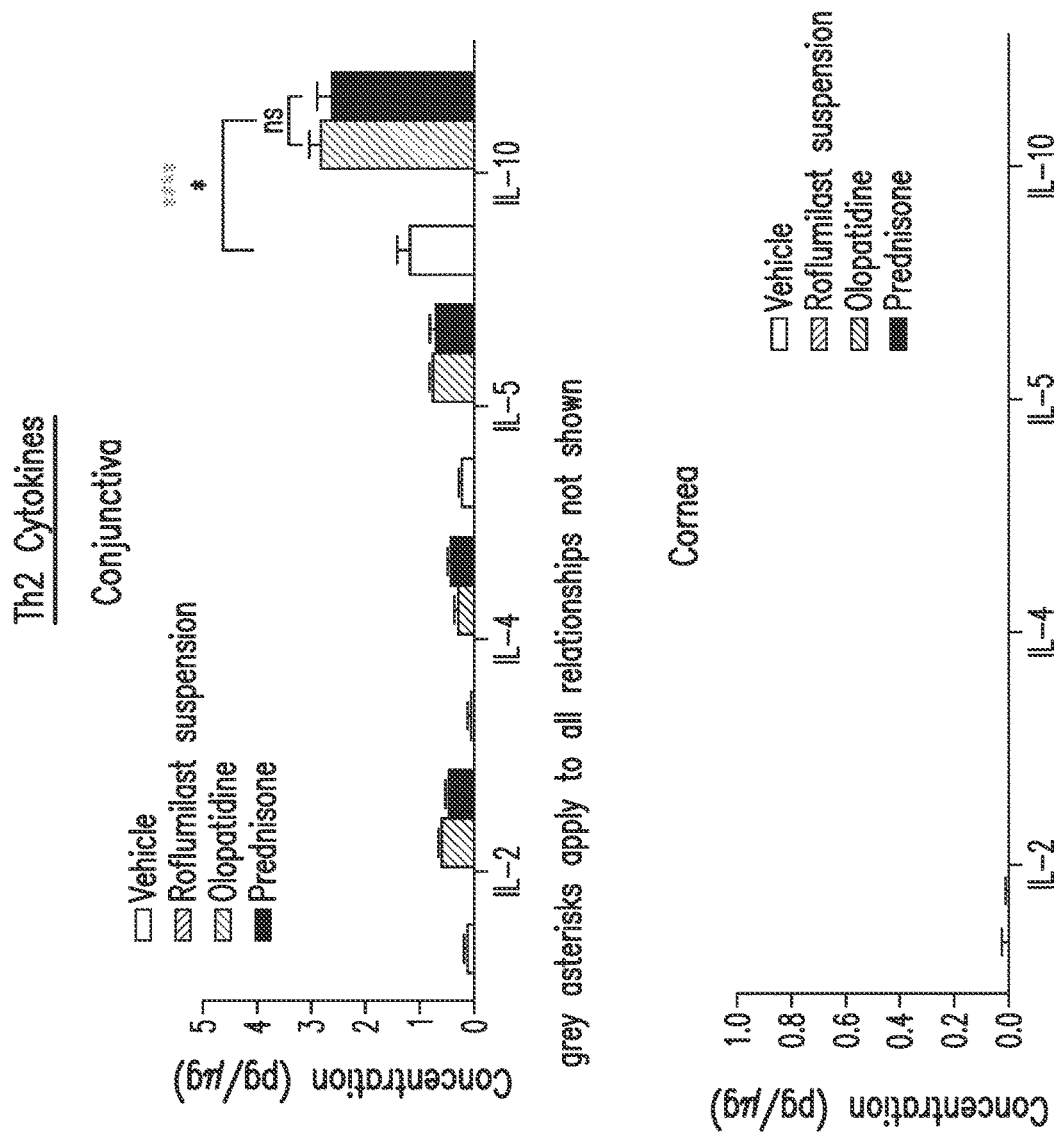
FIG. 6 provides data for the Th2 cytokine response following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.
Figure 7:
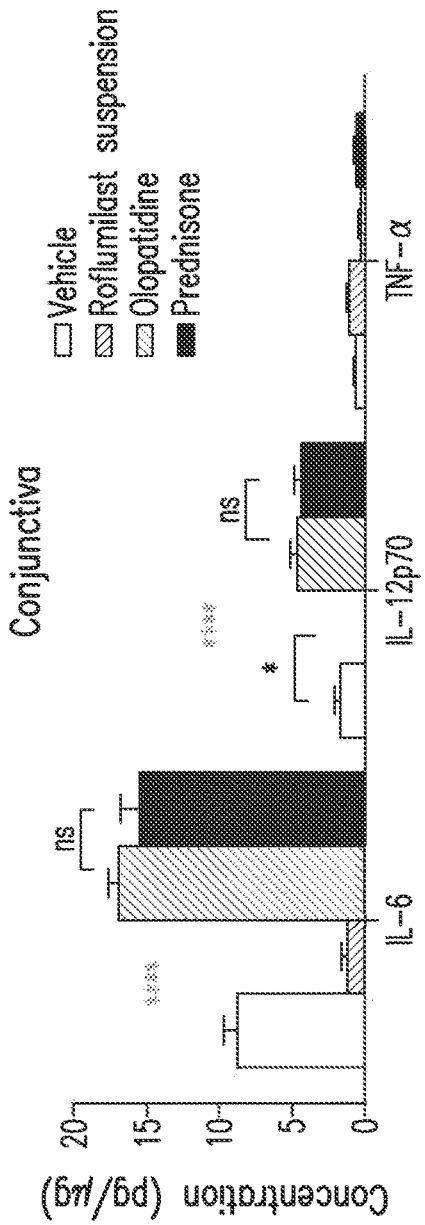
FIG. 7 provides data for the Th17 (IL-6) and Th1 (IL-12p70 and TNF-a) cytokine response following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.
Figure 7:
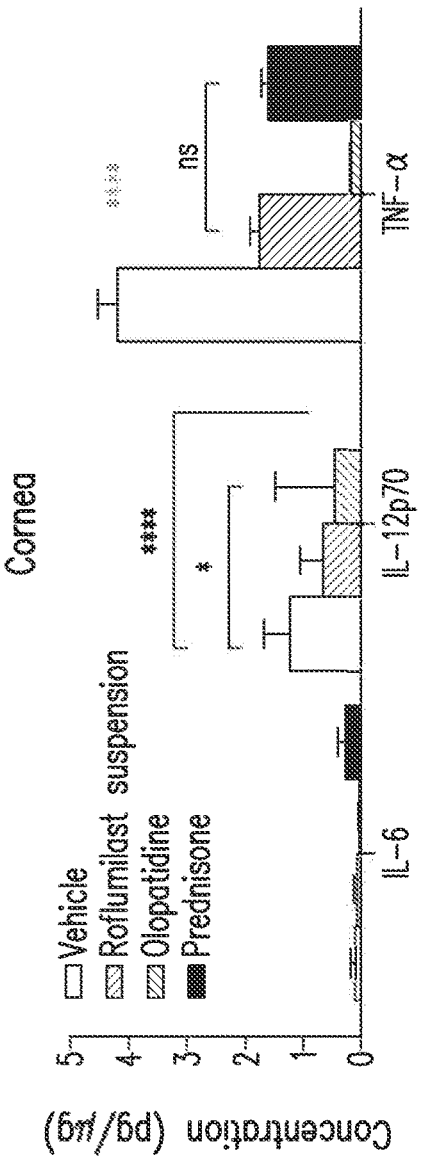
Figure 8:
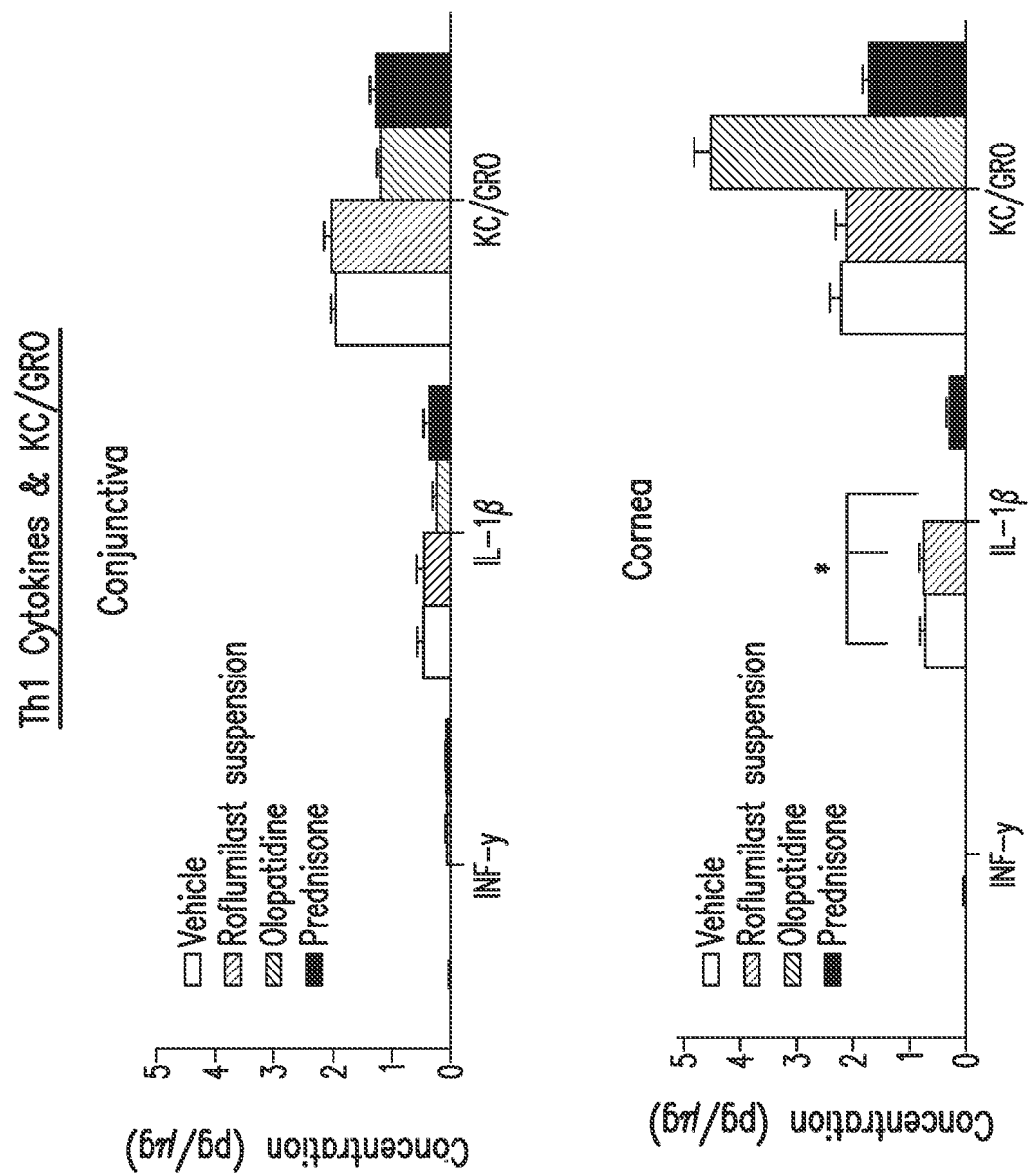
FIG. 8 provides data for the Th1 Cytokine & Chemokine response following administration of roflumilast topical ophthalmic suspension (0.1%), vehicle, prednisolone acetate ophthalmic suspension (1.0%), and olopatadine HCl ophthalmic solution (0.1%) as measured in a murine preclinical model.

As part of the murine preclinical model discussed in Example 9, control of cytokine upregulation as a marker of pharmaceutical control of inflammation was measured following administration of roflumilast topical ophthalmic suspension (0.1%), vehicle, prednisolone acetate ophthalmic suspension (1.0%), and olopatadine HCl ophthalmic solution (0.1%) by comparing level of cytokines in conjunctival and corneal tissue at the end of the experimental timeframe. The results of these cytokine-based inflammation measurements are set forth in FIGS. 6-8 and described below. FIG. 6 illustrates the Th2 cytokine response following administration of roflumilast topical ophthalmic suspension (0.1%), vehicle, prednisolone acetate ophthalmic suspension (1.0%), and olopatadine HCl ophthalmic solution (0.1%) as measured in an animal model study. FIG. 7 illustrates the Th17 cytokine response following administration of roflumilast topical ophthalmic suspension (0.1%), vehicle, prednisolone acetate ophthalmic suspension (1.0%), and olopatadine HCl ophthalmic solution (0.1%) as measured in an animal model study. FIG. 8 illustrates the Th1 cytokine response, as well as that of the chemokine KC/GRO, also known as CXCL1, following administration of roflumilast topical ophthalmic suspension (0.1%), vehicle, prednisolone acetate ophthalmic suspension (1.0%), and olopatadine HCl ophthalmic solution (0.1%) as measured in an animal model study.

The cellular inflammation as measured by terminal cytokine levels was both at a higher absolute level and had more variability between arms than the clinical findings, making it a useful measure of disease response. While the agents of long-term inflammation, the systemic and topical antigen challenges with SRW, were started at day 1 and day 18 respectively, the pharmaceutical treatment in each arm was only started at day 18 of a total of 24 days in each of these experiments, allowing long-term inflammation to build over time before any treatment was given. Yet, in a sample of seven eyes pooled into four samples (pooled to ensure sufficient cytokine concentration), only the roflumilast-treated animals had a non-detectable cytokine level in all four samples of all four cytokines of the conjunctiva associated with Th2 response (the main tissue and mechanism of response for the underlying allergic conjunctivitis disease state of the model)—i.e., IL2, IL4, IL5, and IL10. In this terminal value assay, a non-detectable level meant that the cytokine was either not present in the model or in that tissue, or the agent was successful in reducing that cytokine to below the limit of measurability, fully down-regulating that particular cytokine. The higher the relative level of the cytokine, as measured in pg/µg of relevant tissue, the higher inflammatory impact that cytokine would have on the ocular tissue. The goal of treatment was to lower the cytokine to non-detectable or as close as possible, and to understand in which tissue the inflammatory targets were most relevant. The standard of care treatments for this disease, traditionally known to have either a quick response (e.g., olopatadine) or a profound and lasting response (e.g., corticosteroid), had significantly higher residual levels of cytokines, with less control of their inflammatory impact on disease, in the conjunctiva Th2 cytokine samples. In the Th17 and Th1 cytokines, two of the known primary mechanisms of PDE-4 inhibition, roflumilast had a highly significant impact ($p<0.0005$) for IL-6 and IL-12p70 in the conjunctiva vs steroid and antihistamine (significant as well vs vehicle), and not stastically different vs corticosteroid (in TNF-α in the conjunctiva and IL-6 and TNF-α in the cornea, a tissue not directly related to the model, suggesting cytokine trafficking across the tissues of the eye. The agent also saw similar levels of cytokines and chemokine regulation as olopatadine and corticosteroids in Th1 cytokines which are typically tied to early-phase allergic mast-cell driven response (as evidenced by the strong response of IL-1b to olopatadine in the cornea). Corticosteroids, which are known for their impact on Th1 pathways, showed a highly significant downregulation effect in corneal tissue on IL-12p70, which is relevant in Th1 activation.

Th2 cytokines are particularly important for allergic and short- to mid-term inflammatory disease due to their activation of B cells which are adapted from defense against parasites triggering IgE via IL-4, eosinophil dependent inflammation typically triggered by IL-5, and mast-cell proliferation and the degranulation cascade (IL3/IL4). Th17 driven cytokine response is an important driver of autoimmune signaling and CD4+ effector response, and as such highly relevant to autoimmune and immune-mediated diseases (including many ocular diseases) which typically display both Th17 and Th1 cytokine upregulation which appears to be a particularly inflammatory combination. IL-17, IL-17F, IL6, IL-22, and TNF-α are important T-cell drivers of tissue inflammation and the activation and recruitment of neutrophils. Th1 cytokines, such as IL-1, INF-γ, and TNF-β can alone be important in diseases of autoimmune origin, though they are also often upregulated when protecting against infectious agents and macrophage infiltration (Kaiko et al., Immunology 2008). Th2 and Th17 cytokines have been implicated in inflammatory driven diseases including inflammatory diseases of the eye (Sakkas 2017). Both Tan et al (2014) and Liu et al (2017) investigated the correlation of the Th17 cytokines with various forms of dry eye disease and found increasing agreement and good correlation in etiology of dry eye disease as highly associated with inflammatory drivers, such as elevated cytokines from Th17 cell cascade. Additionally, they found that higher levels of Th17 cytokine expression correlated with clinical severity markers of dry eye such as OSDI, Schirmer test, CFS, etc. Thus, there is wide ranging support that cytokine upregulation of all the Th17, Th1, and Th2 cytokines are a good indicator of inflammation in ocular disease; that cytokine related inflammation is correlated with disease severity; and that the ability to down-regulate these cytokines may be an effective tool in the control of these diseases. Because cytokine involvement is tied to worsening severity of disease, cytokine downregulation is a reasonable therapeutic goal and a positive outcome of the study mentioned in this application. In Example 14, the inventors surprisingly found the cytokine measurements a better endpoint to observe and estimate inflammation and immune-activation in the murine model as well as the immune-control and anti-inflammatory success of the agents tested, and that the agent roflumilast outperformed corticosteroids and antihistamines in down-regulating several key cytokines known to be relevant to a large number of ocular diseases.

Additionally, although this study was undertaken in an allergic conjunctivitis model, the addition of the systemic challenge run-in adapted the study to provide observations mimicking longer-term inflammatory and immune-mediated ocular stress. As such, these cytokine results have applicability to numerous other diseases. Although Examples 13 and 14 relate to a model of allergic conjunctivitis, and as such cytokine upregulation was highest in the conjunctiva with Th2 cytokines, corneal involvement was also seen in the study. The observed Th2 and Th17 cytokine effects in this study are suggestive of potential impact across a wide range of relevant ocular diseases. Many ocular diseases have broad cytokine markers of involvement and severity including demodex blepharitis (Th17: IL-7, IL-12, IL-17; Kim et al., 2010), uveitis associated with JIA (Th17; Walschield, 2019), ocular graft vs. host disease post allogeneic stem cell transplant (IFN-γ (early), IL-6 (late); Riemens 2012) and recurrent herpetic stromal keratitis (Th17/Th1; Rajasagi 2019).

Surprisingly, the inventors of the subject application have discovered that roflumilast administered, topically rather than systemically, in a small and convenient dose, provides a potent response to the IL-6 and IL-12 cytokines of importance to Th17 and IL-2, IL-4, and IL-5 related to Th2 driven inflammation. The results in Example 14 suggest that roflumilast has a broad range of immunomodulatory and anti-inflammatory effects relevant to a number of ocular diseases, again suggesting the agent can be similarly or more efficacious than other common immunomodulatory, immunosuppressive, and anti-inflammatory agents, yet with a better safety and convenience profile.

Example 11

A study was conducted to evaluate the ocular tolerability of repeat topical ocular administration in exaggerated dosing concentration and/or frequency of 1% roflumilast in an ointment formulation (Example 6), or 0.1% roflumilast in two suspension formulations (Examples 1 and 3) in the male Dutch Belted rabbit (n=3 per group). Vehicle arms were not included. The test materials were provided ready for use, the dose volume was 40 µL per eye, and the suspensions were shaken before dose administration. Cohort A received BID administration of the ointment (Example 6) or QID administration of the suspensions (Examples 1 and 3) to test tolerability at exaggerated dosing frequency, ie more than expected clinical dosing frequency. Parameters evaluated included mortality/morbidity, clinical observations, body weights, ophthalmic exams including slit lamp biomicroscopy with Hackett-McDonald scoring and indirect ophthalmoscopy performed by a board-certified veterinary ophthalmologist, and ocular histopathology. Sections of 5 µm thickness were prepared (5 slides per eye) for each eye. Central sections of each globe, including the optic nerve and visual streak, were stained with hematoxylin and eosin (H&E) and examined using light microscopy. Ocular examinations (OEs) were performed at baseline and on Days 1, 3, and 5. Eyes were collected for histopathology at approximately 30 minutes to 1 hour after the last dose on Day 5.

Bilateral BID administration of 1% Roflumilast Ophthalmic Ointment (Example 6) for 5 days resulted in findings of mild to moderate blepharitis on Day 5. Bilateral QID administration of 0.1% Roflumilast Ophthalmic Suspension in either the HPMC (Example 1) or PVP (Example 3) formulations were well tolerated, with no findings observed during the ophthalmic exams including: hyperemia, chemosis, discharge, opacity, cornea pannus, pupillary light reflex, aqueous flare or cells, vitrous cells, or choroidal, retinal, or optic nerve pathology. Additionally, all animals maintained body weight or gained a normal amount of body weight over a 5-day period.

Histopathology assessment showed that ⅙ eyes that received 1% ointment (Example 1) and 3/6 eyes that received 0.1% Roflumilast Ophthalmic Suspension in PVP formulation (Example 3) had mild increased mononuclear cells at the limbus. No other abnormalities were noted in any eye. The infiltrate at the limbus was mild and within normal variation; therefore, no test article-related adverse ocular pathology was observed in this cohort. Additionally, no histopathological signs were seen of cataract, retinal detachment, or retinal degeneration.

These data demonstrate that 1% roflumilast ointment (Example 6) and 0.1% roflumilast suspensions (Examples 1 and 3) were well tolerated even when administered in an exaggerated frequency 2 or 4 times daily (respectively) for 5 days in the Dutch Belted rabbit. The roflumilast ointment (Example 6) induced mild inflammation in the eyelid, but this was not considered adverse.

Example 12

A study was conducted to evaluate the ocular tolerability of 0.1% roflumilast ointment (Example 5) in the New Zealand White rabbit or a higher range of concentrations of the roflumilast suspension than studied in the previous study (0.3%, 1%, or 3%) (Examples 1 and 3) in the Dutch Belted rabbit. The rabbits (n=3 per group) received QD administration of roflumilast or placebo ointment or QID administration of roflumilast suspensions. The dose volume was 40 µL per eye, and the suspensions were shaken before dose administration. Parameters evaluated included mortality/morbidity, clinical observations, body weights, ophthalmic exams including slit lamp biomicroscopy with Hackett-McDonald scoring and indirect ophthalmoscopy performed by a board-certified veterinary ophthalmologist, and ocular histopathology. Sections of 5 µm thickness were prepared (5 slides per eye) for each eye. Central sections of each globe, including the optic nerve and visual streak, were stained with H&E and examined using light microscopy. OEs were performed at baseline and Days 1, 3, and 5. Eyes were collected for histopathology at approximately 45 minutes to 6.5 hours after the last dose on Day 5.

Unilateral once-daily administration of 0.1% Roflumilast Ophthalmic Ointment (Example 5) induced mild blepharitis in ⅓ eyes on Day 5; this finding was not observed in the contralateral placebo eye. Bilateral QID administration of 0.3%, 1%, or 3% Roflumilast Ophthalmic Suspension (Examples 1 and 3) was well tolerated, with no findings observed during the ophthalmic exams, including: hyperemia, chemosis, discharge, opacity, cornea pannus, pupillary light reflex, aqueous flare or cells, vitrous cells, or choroidal, retinal, or optic nerve pathology. Additionally, all animals maintained body weight or gained a normal amount of body weight over a 5-day period.

Histopathology assessment showed that mild mononuclear inflammatory cell infiltrate at the limbus and in the ciliary body was present in one eye treated with 0.1% ointment (Example 5) and one eye that received the placebo ointment. Treatment with 0.3% Roflumilast Ophthalmic Suspension resulted in one suspension eye (Example 3) with mild/focal subconjunctival mononuclear cell infiltrate and one suspension eye (Example 1) with a few mononuclear cells in the vitreous. Multiple eyes that received 1% and 3% Roflumilast Ophthalmic Suspension showed mild mononuclear inflammatory cell infiltrate at the limbus and in the subconjunctival area. The severity was low, but the incidence appeared to increase at the high dose. No difference in this mild inflammation was observed between the two suspension vehicles. Additionally, no histopathological signs were seen of cataract, retinal detachment, or retinal degeneration. Therefore, no test article-related adverse ocular pathology was observed in this cohort.

Example 13

Figure 9:
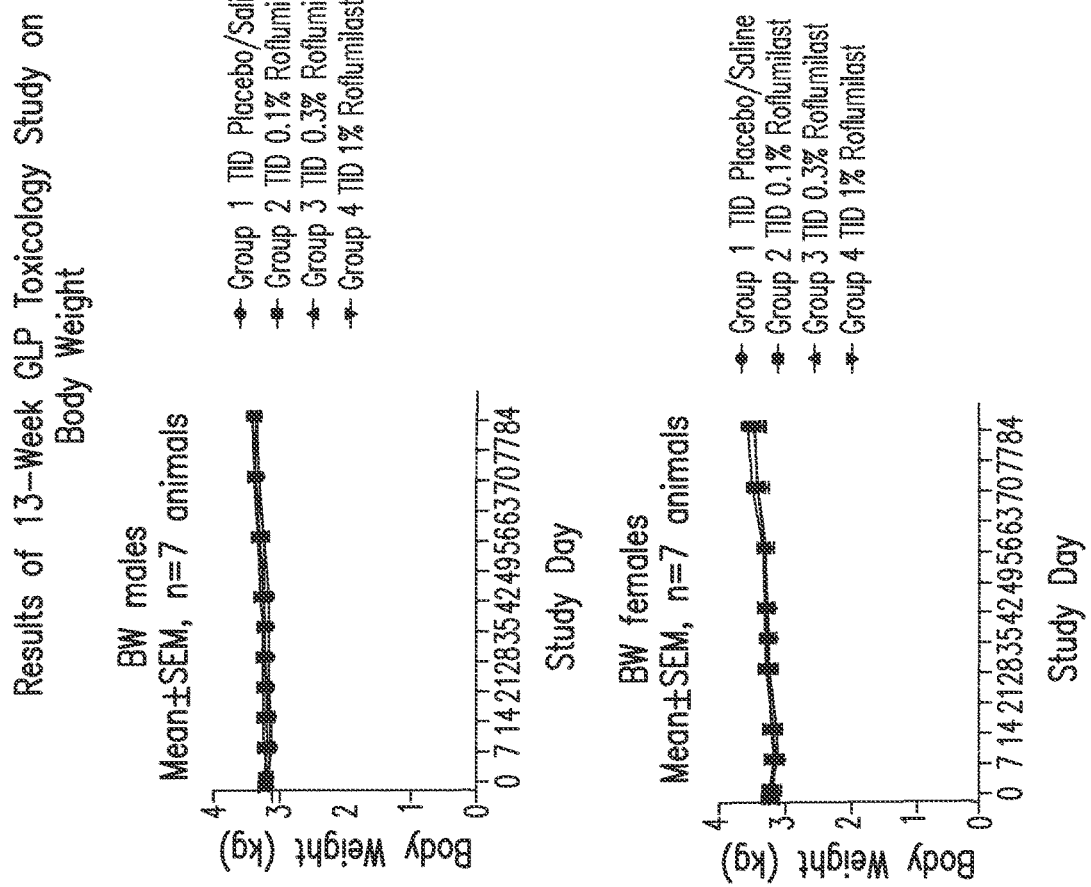
FIG. 9 provides the results of a 13-week GLP toxicology study on body weight following administration of roflumilast topical opthalmic suspensions (0.1%, 0.3%, 1.0%) and placebo/vehicle.
Figure 10:
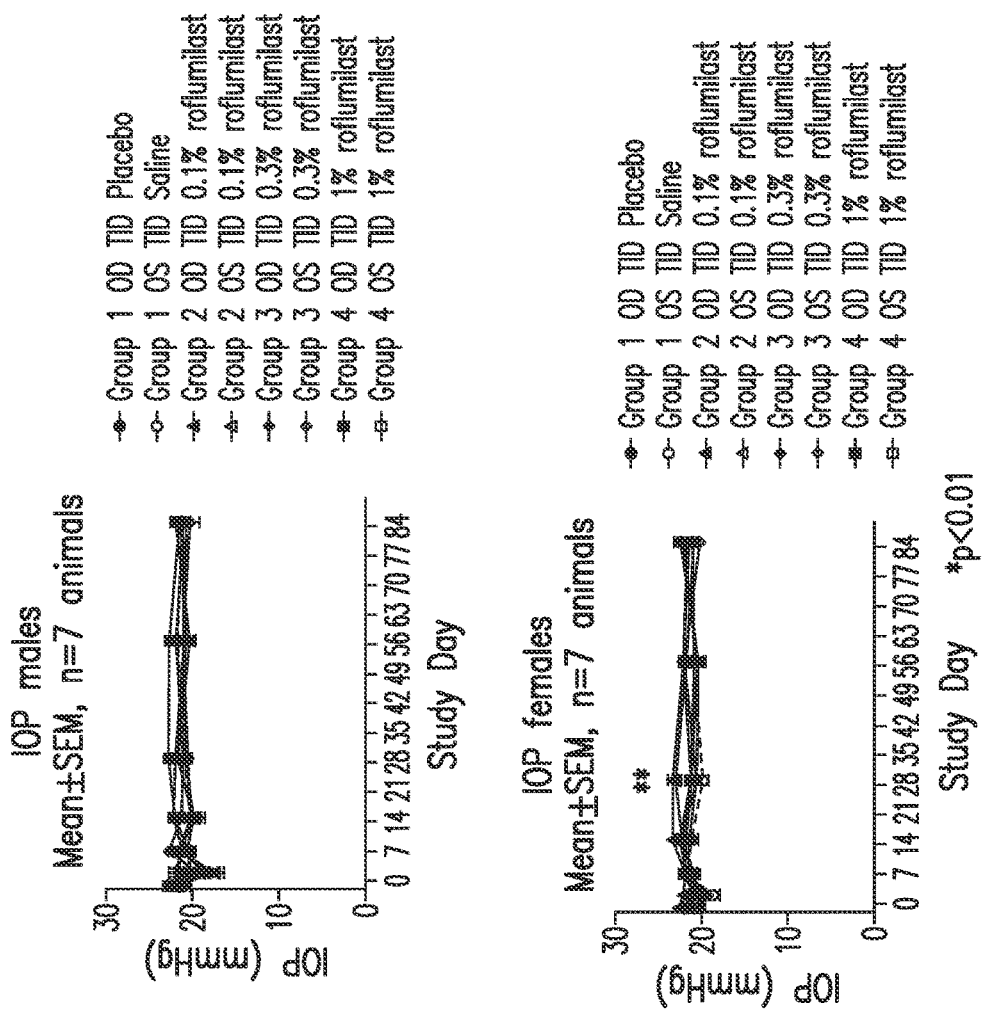
FIG. 10 provides the results of a 13-week GLP toxicology study on intra-ocular pressure (TOP) following administration of roflumilast topical opthalmic suspensions (0.1%, 0.3%, 1.0%) and placebo/vehicle.
Figure 11:
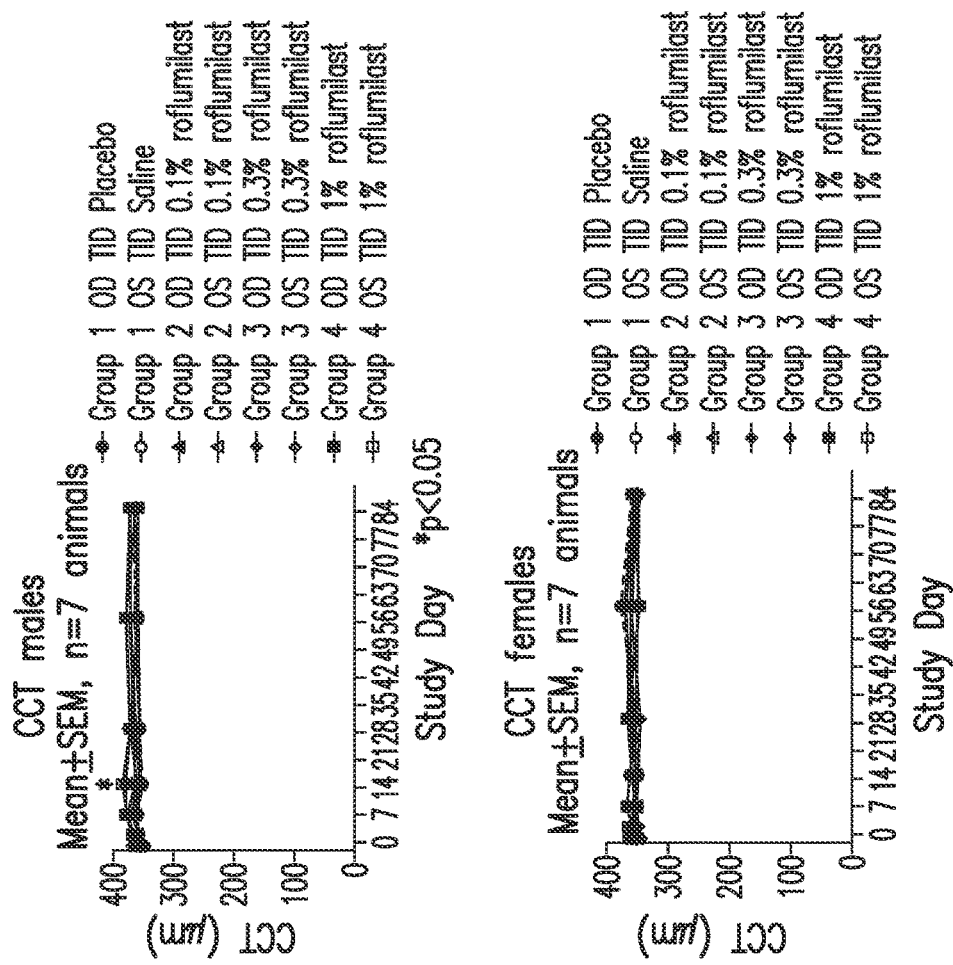
FIG. 11 provides the results of a 13-week GLP toxicology study on central corneal thickness (pachymetry) following administration of roflumilast topical opthalmic suspensions (0.1%, 0.3%, 1.0%) and placebo/vehicle.

To further test the tolerability and safety of roflumilast topical ophthalmic suspension over an extended dosing range and frequency, and an extended dosing period, similar to the dosing length which would be used in a human clinical trial, the pharmaceutical composition was utilized in a GLP-toxicology study of 13-weeks of treatment in rabbits. Either 0.1%, 0.3%, or 1.0% concentrations of the roflumilast topical ophthalmic suspension (Example 3, Table 3), or a control (either saline or vehicle of the same roflumilast topical ophthalmic suspension (Example 1, Table 1, minus any active drug) were given to New Zealand White Rabbits TID (three times per day) over the course of 13 weeks, followed by a 4 week recovery period. Both male and female animals were tested, with n=7 animals in each sex/dose group, for a total of n=56. Animals were assessed for clinical observations, morbidity/mortality, body weight, food consumption, intraocular pressure, corneal thickness, ophthalmic examinations with McDondald-Shadduck scoring, electroretinograms (ERG), clinical pathology (hematology, coagulation, clinical chemistry), systemic exposure, organ weights, and ocular and systemic histopathology. Three areas of particular interest studied were known human side effects of standard of care anti-inflammatory agents, albeit with some inter-species differences. The animals were evaluated at regular intervals, in both eyes, for changes in intraocular pressure (TOP), corneal thickness, and for overall weight change as a surrogate for overall wellness and health of the animal. As shown in FIGS. 9-11, in Example 13, no test-article effect was seen on body weight, TOP, or central corneal thickness (pachymetry) throughout the duration of the study. FIG. 9 provides the results of the study on body weight. FIG. 10 provides the results of the study on TOP. FIG. 11 provides the results of the study on central corneal thickness (pachymetry). Notably, there were no TOP spikes in any eye noted in TOP, and although there were some transient changes in TOP or corneal thickness in certain eye or sex groups, none were considered adverse.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A method for treating a patient having an ocular inflammatory or immune-mediated disorder, comprising:
   administering a stable ophthalmic pharmaceutical suspension comprising a therapeutically effective amount of between 0.1% w/v to 3.0% w/v of roflumilast or a pharmaceutically acceptable salt thereof, an amount of a viscosity agent between 0.1% w/v and 5.0% w/v, an amount of a surfactant between 0.05% w/v and 3.0% w/v, and an amount of a buffer between 0.1% w/v and 5.0% w/v to an ocular surface of said patient,
   wherein said administration results in a reduction of at least one side effect relative to administration of an immunosuppressant, immunomodulatory, or a non-steroidal anti-inflammatory agent,
   wherein a pH of said stable ophthalmic pharmaceutical suspension is between 6.0 and 6.7.

2. The method of claim 1, wherein the immunosuppressant immunomodulatory, or a non-steroidal anti-inflammatory agent is an ophthalmic prednisolone topical composition.

3. The method of claim 1, wherein said side effect is an ocular side effect selected from the group consisting of: increase of intraocular pressure, thinning of corneal, scleral and epithelial tissue, perforation of corneal, scleral and epithelial tissue, delayed or decreased wound or epithelial healing, defects in vision, burning, stinging, foreign body sensation, hyperemia, lid edema, pain, ocular pruiritis, urticarial, rash, allergic reactions, keratitis, conjunctivitis, posterior subcapsular cataract formation, glaucoma, optic nerve damage, corneal ulcers, mydriasis, defects in vision, burning, stinging, foreign body sensation, increased susceptibility to fungal, bacterial, or viral infections, reactivation of fungal or viral infections, masking of acute purulent infections, increased bleb formation after surgery, dry eye, punctate keratopathy, central serous chorioretinopathy, ophthalmicus medicamentosa, loss of accommodation, ptosis, acute anterior uveitis or perforation of the globe.

4. The method of claim 1, wherein said side effect is a systemic side effect selected from the group consisting of change in blood glucose, weight gain or loss, decreased systemic wound healing, susceptibility to systemic microbial infections, irritation to tissues surrounding the eye, cold syndrome, pharyngitis, asthenia, back pain, headache, cough, nausea, rhinitis, sinusitis, osteoporosis, and taste perversion or dysgeusia, or sulfite-related anaphylaxis.

5. The method of claim 1, wherein said administration results in a reduction of dose frequency or other measure of dosing convenience relative to the administration of the immunosuppressant, immunomodulator, or a non-steroidal anti-inflammatory agent.

6. The method of claim 1, wherein the administration downregulates cytokine or chemokine activity driven by inflammatory stress in at least one eye tissue selected from the group consisting of corneal and conjunctival tissue.

7. The method of claim 1, wherein the administration results in disease-modifying activity in at least one supportive tissue or gland of the patient selected from the group consisting of: the cornea, the conjunctiva, the Meibomian gland, the iris, the uvea, the retina, or the choroid.

8. The method of claim 1, wherein said ocular inflammatory or immune-mediated disorder is an ocular surface disease selected from the group consisting of: post-operative pain and inflammation from cataract or other ocular surgery or laser therapy, post-corneal refractive surgery haze, post-operative full or partial thickness corneal transplantation, dry eye syndrome including Sjogren's or other autoimmune or inflammatory dry eye disease, evaporative or desiccative dry eye disease, ocular graft vs host disease, ocular rosacea, allergic conjunctivitis or keratoconjunctivitis, keratitis, atopic keratoconjunctivitis, vernal keratoconjunctivitis, keratitis, herpetic or viral keratitis including herpetic or viral stromal keratitis/herpetic or viral blepharitis or conjunctivitis, Zoster related inflammation, inflammation secondary to other infectious agents, including bacterial, viral, or fungal infections, inflammation secondary to ocular chemical burns, ocular Stevens-Johnson syndrome/TENS, uveitis including uveitis of juvenile idiopathic arthritis, seborrheic or other forms of blepharitis, limbal stem cell deficiency Meibomian gland dysfunction, episcleritis, pingueculitis, and pterygia, phlyctenulosis, staphylococcal hypersensitivity, Mooren's ulcer, endotheleitis, superior limbic keratoconjunctivitis, or another ocular condition traditionally treated with steroids where patients are contra-indicated due to a history of intra-ocular pressure, wound healing, or fungal or other microbial infections.

9. The method of claim 1, wherein said ocular inflammatory or immune-mediated disorder is an anterior or posterior ocular disease selected from the group consisting of: anterior-, pan-, and posterior uveitis (infectious or non-infectious), diabetic retinopathy, diabetic macular edema, geographic atrophy, dry or wet age-related macular degeneration, retinal vein occlusion, drug related/iatrogenic, non-infectious/sterile, or idiopathic retinal vasculitis, endothalmitis, or retinitis, ocular manifestations of Bechet's disease, or other retinal or anterior diseases.

10. The method of claim 1, wherein said ocular inflammatory or immune-mediated disorder is dry eye disease, uveitis, or herpetic or viral keratitis.

11. A method for treating a patient having an ocular inflammatory or immune-mediated disorder, comprising:
administering a stable ophthalmic pharmaceutical suspension comprising a therapeutically effective amount of between 0.1% w/v to 3.0% w/v of roflumilast or a pharmaceutically acceptable salt or metabolite thereof, an amount of a viscosity agent between 0.1% w/v and 5.0% w/v, an amount of a surfactant between 0.05% w/v and 3.0% w/v, and an amount of a buffer between 0.1% w/v and 5.0% w/v,
wherein said administration downregulates cytokine activity driven by inflammatory stress in at least one ocular tissue selected from the group consisting of corneal and conjunctival tissue, and
wherein a pH of said stable ophthalmic pharmaceutical suspension is between 6.0 and 6.7.

12. The method of claim 11, wherein the administration results in disease-modifying activity in at least one supportive tissue or gland of the patient selected from the group consisting of: the cornea, the conjunctiva, the Meibomian gland, the sclera, the ciliary body, the iris, the lens, the uvea, the choroid, the retinal pigment epithelium (RPE), or the retina.

13. The method of claim 11, wherein said ocular inflammatory or immune-mediated disorder is an ocular surface disease selected from the group consisting of: post-operative pain and inflammation from cataract or other ocular surgery or laser therapy, post-corneal refractive surgery haze, post-operative full or partial thickness corneal transplantation, dry eye syndrome including Sjogren's or other autoimmune or inflammatory dry eye disease, evaporative or desiccative dry eye disease, ocular graft vs host disease, ocular rosacea, allergic conjunctivitis or keratoconjunctivitis, atopic keratoconjunctivitis, vernal keratoconjunctivitis, keratitis, herpetic or viral keratitis including herpetic or viral stromal keratitis/herpetic or viral blepharitis or conjunctivitis, zoster related inflammation, inflammation secondary to other infectious agents including bacterial, viral, or fungal infections, inflammation secondary to ocular chemical burns, ocular Stevens-Johnson syndrome/TENS, uveitis including uveitis of juvenile idiopathic arthritis, seborrheic or other forms of blepharitis, limbal stem cell deficiency, Meibomian gland dysfunction, episcleritis, pingueculitis, and pterygia, phlyctenulosis, staphylococcal hypersensitivity, Mooren's ulcer, endotheleitis, superior limbic keratoconjunctivitis, or another ocular conditions traditionally treated with steroids where patients are contra-indicated due to a history of intra-ocular pressure, wound healing, or fungal or other microbial infections.

14. The method of claim 11, wherein said ocular inflammatory or immune-mediated disorder is an anterior or posterior ocular disease selected from the group consisting of: anterior-, pan-, and posterior uveitis (infectious or non-infectious), diabetic retinopathy, diabetic macular edema, geographic atrophy, dry or wet age-related macular degeneration, retinal vein occlusion, drug related/iatrogenic, non-infectious/sterile, or idiopathic retinal vasculitis, endothalmitis, or retinitis, ocular manifestations of Bechet's disease or other anterior or posterior compartment diseases.

15. The method of claim 11, wherein said ocular inflammatory disorder is dry eye disease, uveitis, or herpetic or viral stromal keratitis.

16. The method of claim 11, wherein said administration results in a reduction of dose frequency or other measure of dosing convenience relative to administration of an immunosuppressant, immunomodulatory, or a non-steroidal anti-inflammatory agent.

17. A method for treating a patient having an ocular inflammatory or immune-mediated disorder, comprising:
administering a stable ophthalmic pharmaceutical suspension comprising a therapeutically effective amount of between 0.1% w/v to 3.0% w/v of roflumilast or a pharmaceutically acceptable salt or metabolite thereof, an amount of a viscosity agent between 0.1% w/v and 5.0% w/v, an amount of a surfactant between 0.05% w/v and 3.0% w/v, and an amount of a buffer between 0.1% w/v and 5.0% w/v to a said patient,
wherein said administration downregulates cytokine activity in a manner that is superior to the downregulation of cytokines by administration of an immunosuppressant, immunomodulatory, or a non-steroidal anti-inflammatory agent, and
wherein a pH of said stable ophthalmic pharmaceutical suspension is between 6.0 and 6.7.

18. The method of claim 17, wherein the immunosuppressant, immunomodulatory, or non-steroidal anti-inflammatory agent is an ophthalmic prednisolone topical composition or an anti-histamine olopatadine topical composition.

19. The method of claim 1, wherein the stable ophthalmic pharmaceutical suspension is free of a preservative.

20. The method of claim 11, wherein the stable ophthalmic pharmaceutical suspension is free of a preservative.

21. The method of claim 17, wherein the stable ophthalmic pharmaceutical suspension is free of a preservative.

* * * * *